United States Patent
Bergendahl et al.

(10) Patent No.: US 9,345,626 B2
(45) Date of Patent: May 24, 2016

(54) METHOD FOR PRODUCING A WEB OF A LAMINATE MATERIAL FOR RETAINING FAECES AND METHOD FOR PRODUCING AN ABSORBENT ARTICLE

(75) Inventors: Magnus Bergendahl, Mölnlycke (SE); Anna Klinte Olsson, Askim (SE); Niklas Lagergren, Kullavik (SE); Robert Perneborn, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 657 days.

(21) Appl. No.: 13/635,058

(22) PCT Filed: Mar. 18, 2010

(86) PCT No.: PCT/SE2010/050302
§ 371 (c)(1),
(2), (4) Date: Sep. 14, 2012

(87) PCT Pub. No.: WO2011/115537
PCT Pub. Date: Sep. 22, 2011

(65) Prior Publication Data
US 2013/0012898 A1    Jan. 10, 2013

(51) Int. Cl.
*A61F 13/512* (2006.01)
*B32B 38/04* (2006.01)
(Continued)

(52) U.S. Cl.
CPC ..... *A61F 13/15804* (2013.01); *A61F 13/15593* (2013.01); *A61F 13/15699* (2013.01);
(Continued)

(58) Field of Classification Search
CPC ............ Y10T 156/101; Y10T 156/1015; Y10T 156/1026; Y10T 156/1051; Y10T 156/1057; Y10T 156/1062; Y10T 156/1085; A61F 2013/1513; A61F 13/15585; A61F 13/15617; A61F 13/15699; A61F 13/15747; A61F 13/15804; B32B 37/02; B32B 37/12; B32B 37/20; B32B 2038/045
See application file for complete search history.

(56) References Cited

U.S. PATENT DOCUMENTS

| | | | |
|---|---|---|---|
| 5,342,338 A | | 8/1994 | Roe |
| 5,554,243 A | * | 9/1996 | Igaue et al. ................... 156/164 |

(Continued)

FOREIGN PATENT DOCUMENTS

| | | |
|---|---|---|
| EP | 1 132 071 | 9/2001 |
| EP | 1 346 712 | 9/2003 |

(Continued)

OTHER PUBLICATIONS

Extended European search report issued Jun. 8, 2015 in corresponding European Application No. 10848077.3 (6 pages).

*Primary Examiner* — Linda L Gray
(74) *Attorney, Agent, or Firm* — Drinker Biddle & Reath LLP

(57) ABSTRACT

A method for producing a web of a laminate material for retaining faeces including laminating first and second webs to form an intermediate laminate web, providing transversal slits in the intermediate laminate web and expanding the intermediate laminate web such that the slits are opened to openings. An expanded intermediate laminate web is formed by the expansion. The expanded web is laminated to a third web in order to fix the expanded web in an expanded state, whereby the laminate material web is formed. Also, a method of producing an absorbent article including producing the laminate material web according to the method above.

8 Claims, 16 Drawing Sheets

(51) Int. Cl.
  *B32B 37/02* (2006.01)
  *A61F 13/15* (2006.01)
  *B32B 37/14* (2006.01)
  *B32B 37/00* (2006.01)
  *B32B 37/12* (2006.01)

(52) U.S. Cl.
  CPC ........... *A61F13/5123* (2013.01); *B32B 37/144* (2013.01); *A61F 13/15585* (2013.01); *A61F 13/15747* (2013.01); *B32B 37/0084* (2013.01); *B32B 37/12* (2013.01); *B32B 37/1292* (2013.01); *B32B 2037/1215* (2013.01); *B32B 2037/1276* (2013.01); *B32B 2038/045* (2013.01); *B32B 2310/028* (2013.01); *B32B 2555/02* (2013.01); *Y10T 156/101* (2015.01); *Y10T 156/1015* (2015.01); *Y10T 156/1026* (2015.01); *Y10T 156/1051* (2015.01); *Y10T 156/1056* (2015.01); *Y10T 156/1062* (2015.01)

(56) References Cited

U.S. PATENT DOCUMENTS

| | | | |
|---|---|---|---|
| 5,804,021 A * | 9/1998 | Abuto et al. | 156/252 |
| 5,957,907 A | 9/1999 | Sauer | |
| 7,540,862 B2 | 6/2009 | Olsson et al. | |
| 8,741,083 B2 | 6/2014 | Wennerbäck et al. | |
| 2002/0026168 A1 | 2/2002 | Yagou et al. | |
| 2007/0239132 A1 | 10/2007 | Mishima | |

FOREIGN PATENT DOCUMENTS

| | | |
|---|---|---|
| EP | 1 350 498 | 10/2003 |
| EP | 1 227 776 | 1/2007 |
| EP | 1 138 301 | 11/2008 |
| WO | 99/55273 | 11/1999 |
| WO | 01/43968 | 6/2001 |
| WO | 2006/071143 | 7/2006 |
| WO | WO 2007/133128 | 11/2007 |
| WO | 2008/029331 | 3/2008 |

* cited by examiner

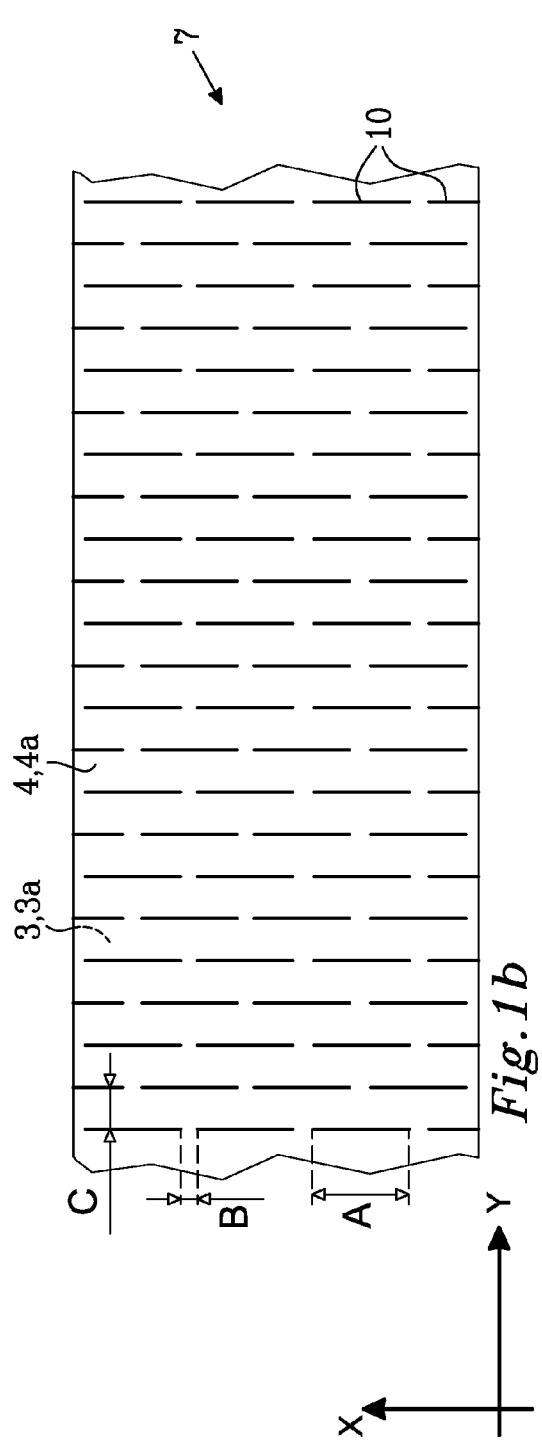
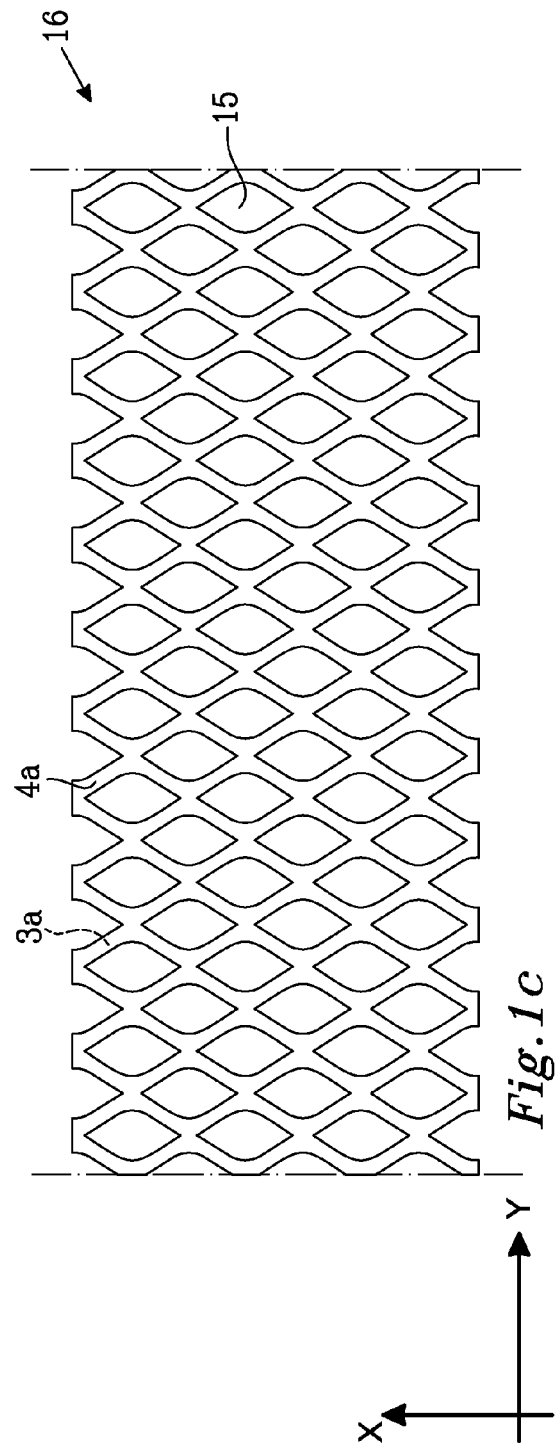
Fig. 1b
Fig. 1c

METHOD FOR PRODUCING A WEB OF A LAMINATE MATERIAL FOR RETAINING FAECES AND METHOD FOR PRODUCING AN ABSORBENT ARTICLE

CROSS-REFERENCE TO RELATED APPLICATIONS

This application is a §371 National Stage Application of PCT International Application No. PCT/SE2010/050302 filed Mar. 18, 2010, which is incorporated herein in its entirety.

TECHNICAL FIELD

The present disclosure relates to a method for producing a web of a laminate material for retaining faeces for use in an absorbent article, such as a diaper, pant diaper, incontinence garment or the like. In addition, the present disclosure relates to a method for producing an absorbent article, such as a diaper, pant diaper, incontinence garment or the like, including a step of producing the web of the laminate material for retaining faeces. Furthermore, the present disclosure relates to a web obtained by the web production method and to an absorbent article obtained by the method for producing an absorbent article.

BACKGROUND

Absorbent articles of the above mentioned kind are intended to absorb and retain body exudates, like urine, faeces and menstrual fluid. Typically, such absorbent articles include an absorbent core sandwiched between a liquid-permeable topsheet and a liquid-impermeable backsheet. Body fluids, especially urine, easily penetrate the liquid-permeable topsheet and are absorbed and retained by the absorbent core. However, body exudates in solid or semi-solid state, such as fecal materials, can normally not penetrate the liquid-permeable topsheet. Thereby, the fecal materials are not isolated within the articles, which results in the fecal materials remaining on the topsheet.

The fact that fecal materials are not isolated within the above mentioned kind of absorbent articles may result in leakage, for example, at the waist regions or the leg openings. In order to reduce the leakage risk, many absorbent articles of the above mentioned kind include means, such as elasticized waistbands and leg cuffs, for inhibiting body exudates in solid or semi-solid state from leaking out of the articles. Furthermore, additional barrier flaps are often provided between the leg openings and the absorbent core to further inhibit leakage.

In addition, the fact that fecal materials are not isolated within absorbent articles, but remain on the topsheet, results in contact between the fecal materials and the skin of the users. It is well-known that contact between fecal materials and the skin of users often give rises to skin irritation and severe discomfort for the users. For example, it may give rise to diaper rash.

It is known to deal with fecal materials by providing a topsheet that conforms closely to the wearer and which has a large aperture that is intended to register with the anal opening, so that fecal material passes through the aperture into a void space, where it is kept isolated from the wearer. Examples of such diapers are shown in U.S. Pat. No. 5,957,907 and WO2008029331

However, these attempts do not solve the problem of handling and retaining low-viscosity fecal material that is prevalent in younger children, especially those who are breast fed, and persons suffering from diarrhea. Low-viscosity fecal material easily moves around on the user facing side of the topsheet under the influence of gravity, motion and pressure by the user. The migration of the fecal material often moves it to the perimeter of the article, increasing the likelihood of leakage, and further smears it against the skin of the user making cleanup more difficult. However, there are different attempts known today trying to solve the problem of handling and retaining low-viscosity fecal material.

One attempt of dealing with low-viscosity fecal matter is described in U.S. Pat. No. 5,342,338, which discloses a topsheet having apertures large enough for low-viscosity fecal material to pass through to a secondary topsheet. The secondary topsheet immobilizes the fecal material in position for dewatering.

Another attempt is described in WO 2006/071143 disclosing an absorbent article having improved properties for handling low-viscosity fecal material. The article includes an inner cover including a three-dimensionally structured hydrophilic fibrous web material having a plurality of recessed and elevated portions. Both the recessed and elevated portions are hydrophilic. Low-viscosity fecal material adheres effectively to the structured hydrophilic fibrous web resulting in immobilization of the faeces. The three-dimensional shaping of the web material may be accomplished by means of e.g. vacuum forming, heat embossing or printing with a bonding agent.

WO 99/55273 describes an apertured laminate web, which may be used as a topsheet in an absorbent article and which is told to be adapted to handle low-viscosity fecal material. The laminate web is formed of first and second liquid pervious materials each having apertures with a defined effective size. The apertures of the first and second materials are aligned and the second material preferably has a hydrophilicity that is greater than the hydrophilicity of the first material. The apertured laminate web is formed by simultaneously bonding and aperturing the first and second materials.

EP 1138301 discloses an absorbent article including an absorbent upper panel attached to an outer surface of a topsheet. The panel is arranged for handling and retaining fecal material, e.g. loose passage, and is made of a fibrous web including a low density fibrous layer that is overlaid by a high density fibrous layer. Also, the panel includes a plurality of openings extending through the thickness. Within the openings, moisture content of loose passage permeates into the topsheet and is absorbed by the core while solid content of loose passage present in the openings permeates into the low density fibrous layer. The fibrous web of the panel may be produced by a process including accumulation of fibres on a moving conveyor provided with a plurality of pins shaped in conformity of the openings.

However, there is still a need for alternative methods for producing a material for retaining faeces, in particular for immobilization of low-viscosity fecal material, which material for retaining faeces is adapted to be used in an absorbent article.

SUMMARY

Accordingly, an object is to provide an alternative method for producing a web of a laminate material for retaining faeces, in particular for immobilization of low-viscosity fecal material, which laminate material for retaining faeces is adapted to be used in an absorbent article.

This can be achieved by the method including the steps of:
 a. providing a first web of a first material for contacting the skin of a user of said absorbent article;

b. providing a second web of a second material, said second material being a volume-forming material;
c. laminating said first web and said second web so as to form an intermediate laminate web, said intermediate laminate web having a longitudinal direction, a transverse direction and a thickness direction;
d. providing a multitude of transversal slits in said intermediate laminate web, each slit extending through said first material and said second material of said intermediate laminate web in said thickness direction;
e. expanding said intermediate laminate web in said longitudinal direction such that said slits are opened to openings for retaining faeces, whereby said expansion provides an expanded intermediate laminate web in the form of a reticulated structure,
f. providing a third web of a third material for fixing said expanded intermediate laminate web such that it is maintained in an expanded state, and
g. laminating said second material of said expanded intermediate laminate web and said third web, whereby said expanded intermediate laminate web is fixed in position in relation to said third web and is fixed in an expanded state, and whereby said laminate material web is formed.

Another object is to provide an improved method for producing an absorbent article including a laminate material for retaining faeces. This can be achieved by the method including the steps of:

producing the laminate material web according to the method for producing a web of a laminate material for retaining faeces according to the disclosure, producing a piece of said laminate material web by cutting along at least one cutting line, whereby said laminate material piece is produced such that it includes a plurality of said openings, providing a liquid permeable topsheet for said absorbent article, said topsheet having a first surface arranged to face said user and a second surface arranged to face away from said user, said topsheet being delimited by borders, and applying said laminate material piece to said topsheet such that said first material of said laminate material piece is arranged to face said user and such that at least a plurality of said openings of said laminate material piece are arranged to be exposed to said user.

In a further aspect, there is provided a web of a laminate material for retaining faeces for use in an absorbent article, which web is obtained by the web production method.

In another aspect, there is provided an absorbent article obtained by means of the method for producing an absorbent article.

Still other objects and features will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views:

FIG. 1b shows a top view of a portion of an intermediate laminate web after provision of transversal slits;

FIG. 1c shows a top view of a portion of the intermediate laminate web after it has been expanded to an expanded intermediate laminate web, i.e. after the slits have been opened to openings;

FIG. 3b is a perspective view of the laminate material piece shown in FIG. 3a;

FIG. 3c shows the portion of the web shown in FIG. 2d after application of the laminate material piece shown in FIG. 3a;

FIG. 5b is a cross-sectional view according to line Vb-Vb in FIG. 5a;

FIG. 7b is a cross-sectional view along line VIIb-VIIb in FIG. 7a.

DETAILED DESCRIPTION OF PREFERRED EMBODIMENTS

As mentioned previously, the disclosure concerns a method for producing a web of a laminate material for retaining faeces for use in an absorbent article. In addition, the disclosure concerns a method for producing an absorbent article. The term "absorbent article" refers herein to a product that is intended to be placed against the skin of a wearer/user in order to absorb and contain body exudates, like urine, faeces and menstrual fluid. In particular, the laminate material produced by means of the method according to embodiments of the invention is adapted to be utilized in an absorbent article in the form of a diaper, pant diaper, incontinence garment or the like. Embodiments of the invention will be described in more detail in the following with reference to the accompanying drawings.

Figure 1A:
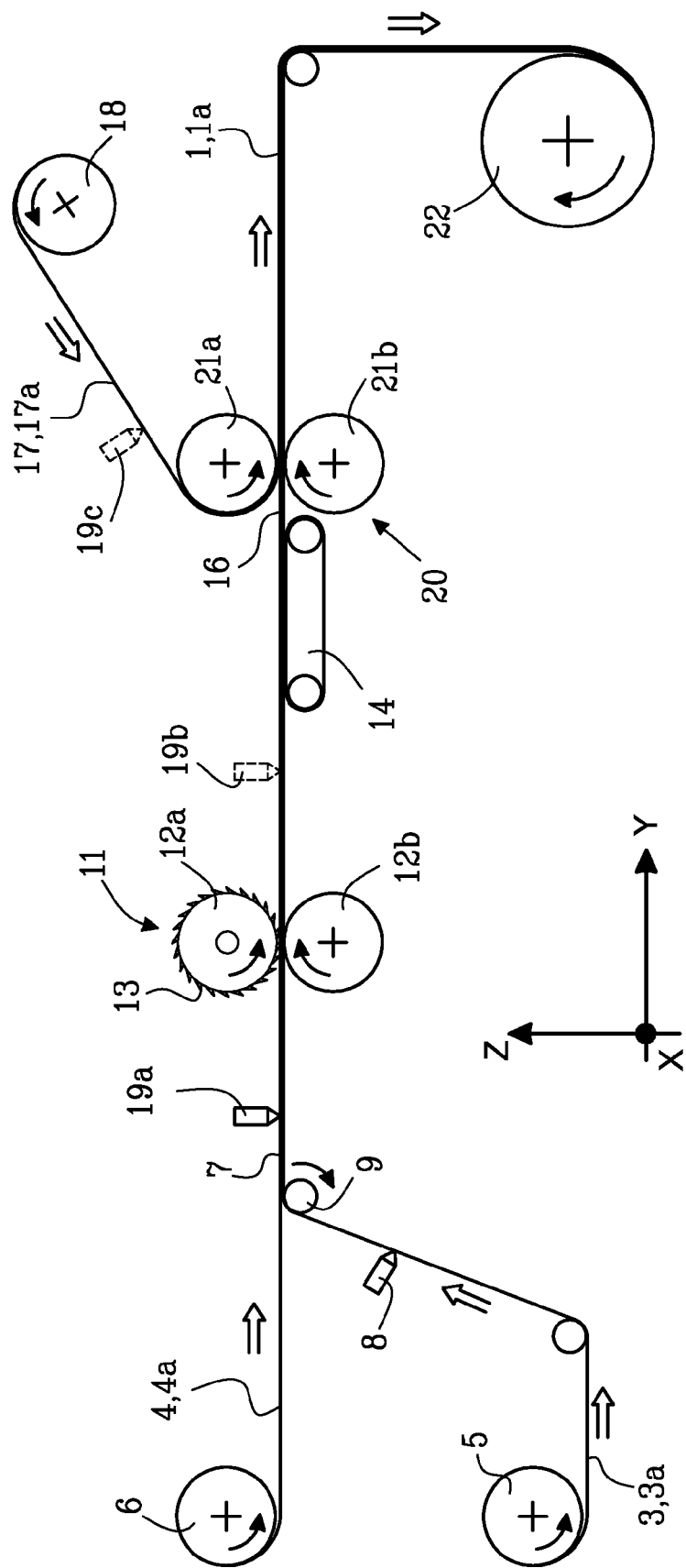
FIG. 1a illustrates schematically one embodiment of the method for producing a web of a laminate material for retaining faeces.
Figure 7A:
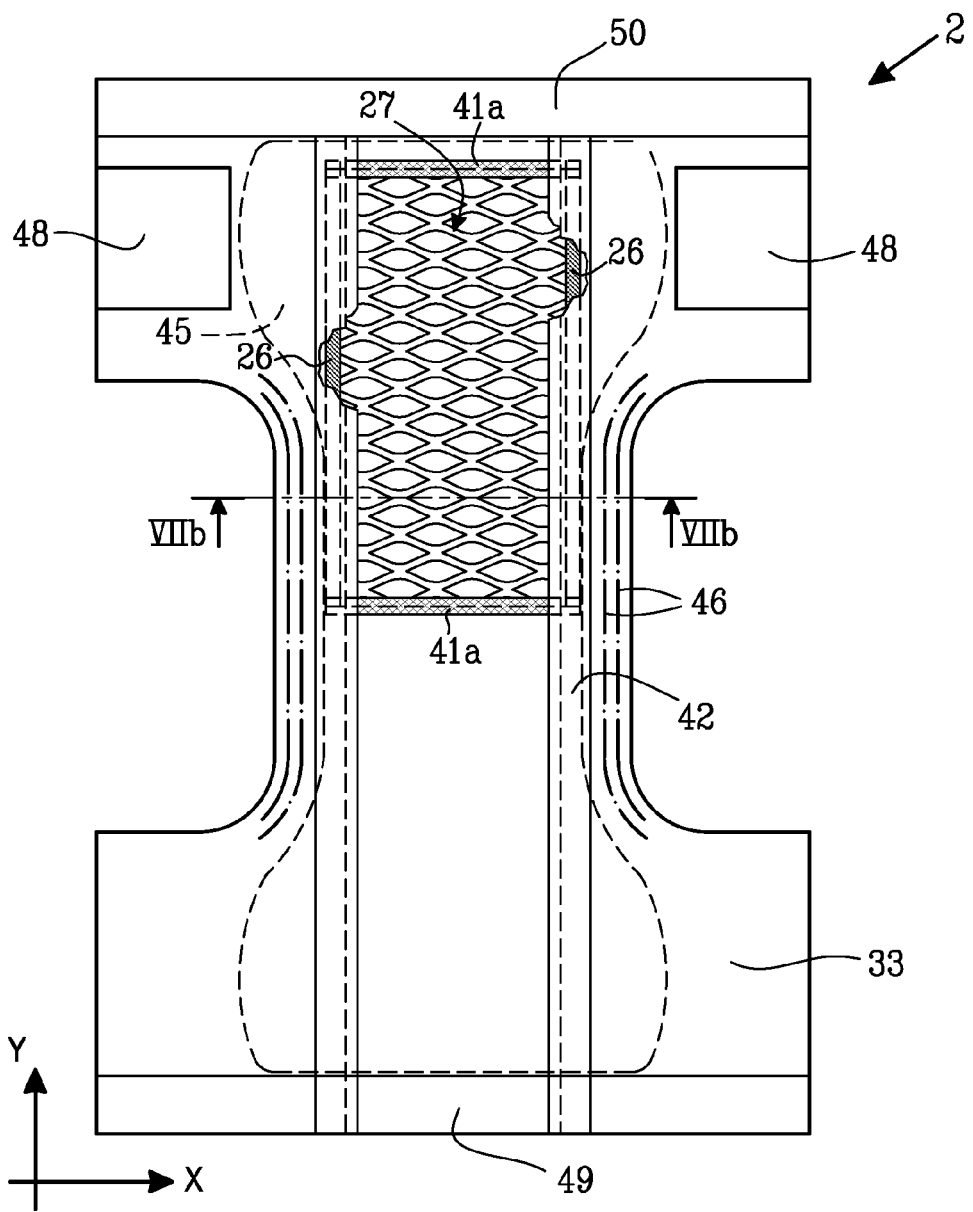
FIG. 7a shows a top view of an absorbent article produced according to the first embodiment.

FIG. 1a illustrates schematically one embodiment of the method for producing a web 1 of a laminate material 1a for retaining faeces, which is intended to be used in an absorbent article 2 (FIG. 7a). A first web 3 of a first material 3a for contacting the skin of a user of the absorbent article 2 is provided into the process and is fed in the direction indicated by the associated arrows. In addition, a second web 4 of a second material 4a, which is a volume-forming material, is provided into the process and is fed in the direction indicated by the associated arrow. As shown in FIG. 1a, the first web 3 and the second web 4 may be provided into the process by being unwound from a first supply roll 5 and a second supply roll 6, respectively. However, instead of being unwound from a supply roll, the first web 3 and/or the second web 4 may be provided directly from a respective forming apparatus into the process. The first and second materials 3a, 4a will be further described below.

The first and second webs 3, 4 are laminated at a first lamination station 9 so as to form an intermediate laminate web 7. In the embodiment shown in FIG. 1a, the lamination of the first and second webs 3, 4 is performed by means of a first adhesive. The first adhesive is applied to the first web 3 by means 8 for application of the first adhesive before the lamination of the first and second webs 3, 4. The means 8 for application of the first adhesive may be constituted by any suitable means for application of adhesive, such as, for example, a slotted glue head or spraying means. Alternatively, the first adhesive may be applied to the second web 4 (not shown) before the lamination of the first and second webs 3, 4. The first adhesive may be applied completely over one of the surfaces of the first web 3 (or the second web 4) or may be applied in any suitable pattern. The first adhesive may be any suitable adhesive for laminating the first and second webs 3, 4. For example, the first adhesive may be a hot melt adhesive, a water-based adhesive or a solvent-based adhesive. Examples of adhesives to be utilized as the first adhesive are Dispomelt 2000 (Henkel), NW 1212 (HB Fuller) and H 9564 (Bostik).

In the embodiment shown in FIG. 1a, the first lamination station 9 is constituted by a first lamination roll, which rotates in the direction indicated by the associated arrow. The first web 3 is fed over the first lamination roll 9 and the second web 4 is fed over the first web 3 such that the second web 4 contacts the first adhesive applied on the first web 3 in order to obtain lamination of the first and second webs 3, 4.

As mentioned above, the first lamination station 9 may be constituted by the above described first lamination roll, but may alternatively include any further or alternative means for laminating the first and second webs 3, 4 by means of the first adhesive. For example, the first lamination station 9 may alternatively include a stationary bar or rod. Furthermore, the lamination of the first and second webs 3, 4 may, instead of being performed by means of the first adhesive, be performed by means of any other suitable bonding technique such as, for example, ultrasonic bonding, thermal bonding or flame lamination. In case ultrasonic bonding, thermal bonding or flame lamination is utilized, the application of the first adhesive is of course omitted and the first lamination station 9 includes any suitable means for performing lamination of the first and second webs 3, 4 by means of ultrasonic bonding, thermal bonding or flame lamination (not shown).

Ultrasonic bonding may be performed using a rotary ultrasonic horn. Thermal bonding may be conducted by passing the first and second webs 3, 4 between two heated rollers. The heated rollers may have smooth surfaces causing lamination over the whole width of the webs 3, 4 or may have pins thereon which form intermittent point bonds between the first and second webs 3, 4. Flame lamination may be performed by passing a flame over one of the webs 3, 4 to heat the surface thereof, which thereby becomes tacky and forms a bond with the other web 3, 4.

As mentioned above, the lamination of the first and second webs 3, 4 forms an intermediate laminate web 7. The intermediate laminate web 7 has a longitudinal direction Y, a transverse direction X and a thickness direction Z when positioned in a plane state as indicated in FIG. 1a. In FIG. 1a the longitudinal direction Y corresponds to the machine direction, the transverse direction X corresponds to the cross machine direction and the thickness direction Z is perpendicular to the machine direction and the cross machine direction.

After the lamination of the first and second webs 3, 4 in order to form the intermediate laminate web 7, a multitude of transversal slits 10 are provided in the intermediate laminate web 7. FIG. 1b shows a portion of the intermediate laminate web 7 after the provision of the transversal slits 10 in a top view with the intermediate laminate web 7 located in a plane state and with the second material 4a located uppermost. The expression "slit provided in the intermediate laminate web" is herein intended to mean an essentially one-dimensional cut in the intermediate laminate web. Thus, each transversal slit 10 is provided such that it extends in the transverse direction X of the intermediate laminate web 7 and through the thickness of the intermediate laminate web 7 in the thickness direction Z, i.e. through both the first material 3a and the second material 4a of the intermediate laminate web 7 in the thickness direction Z.

In the embodiment shown in FIG. 1a, the multitude of transversal slits 10 are provided by means of slit forming means 11 including a knife roll 12a and an anvil roll 12b, which rotate in the direction of the respective associated arrows. The knife roll 12a includes a plurality of knives 13 on its outer surface. The intermediate laminate web 7 is fed between the knife roll 12a and the anvil roll 12b, whereby the knives 13 on the knife roll 12a provide the slits 10 according to a predetermined pattern in the intermediate laminate web 7 located between the knife roll 12a and the anvil roll 12b. However, any other suitable slit forming means than the knife roll and anvil roll may be utilized for the provision of the slits 10. In addition, the knife roll 12a and the anvil roll 12b may change places.

As shown in FIG. 1b, the provided slits 10 may be straight, but may have any suitable shape such as, for example, wave-shaped. Furthermore, as also shown in FIG. 1b, the slits 10 may be provided in a regular pattern in rows extending in the transverse direction X. Alternatively, the slits 10 may, however, be provided in an irregular pattern.

More specifically, in FIG. 1b the slits 10 are provided in staggered rows extending in the transverse direction X. In case the slits 10 are provided in a regular pattern in rows extending in the transverse direction X, e.g. in staggered rows extending in the transverse direction X as shown in FIG. 1b, slits 10 provided non-adjacent any border of the first material 3a or the second material 4a may, for example, be provided to have a slit length A of 5-60 mm, preferably 15-40 mm, in the transverse direction X of the intermediate laminate web 7. Furthermore, the slits 10 may then be provided such that a slit distance B is, for example, smaller than 1 times the slit length A, preferably 0.1-0.5 times the slit length A. In addition, the slits 10 may then be provided such that a row distance C between two adjacent rows is, for example, smaller than 1 times the slit length A, preferably 0.05-0.5 times the slit length A. Furthermore, the slits 10 may then be provided such that a quotient between the slit length A and the row distance C is within the interval 0.1<A/C<2.

The slit length A is herein defined as the length of a slit 10 in the transverse direction X of the intermediate laminate web 7 when it is positioned in a plane state. The slit distance B is herein defined as the distance between the ends of two mutually sequential slits 10 in the transverse direction X of the intermediate laminate web 7 when it is positioned in a plane state. The row distance C is herein defined as the distance between two adjacent rows in the longitudinal direction Y of the intermediate laminate web 7 when it is positioned in a plane state.

Thus, in the embodiment shown in FIG. 1a, the knives 13 of the knife roll 12a may have a length in the cross-machine direction that corresponds to the above specified slit length A. Likewise, the distance between the knives 13 of the knife roll 12a may correspond to the above specified slit distance B and row distance C.

After the provision of the transversal slits 10, the intermediate laminate web 7 is expanded (i.e. stretched or extended) in the longitudinal direction Y such that the slits 10 are opened to openings 15 for retaining faeces (FIG. 1c). By means of the expansion the intermediate laminate web 7 is transformed into an expanded intermediate laminate web 16, i.e. an expanded intermediate laminate web 16 is provided by means of the expansion. The expanded intermediate laminate web 16 has the form of a reticulated structure or grid structure. FIG. 1c shows a portion of the intermediate laminate web 7 after it has been expanded to an expanded intermediate laminate web 16, i.e. after the slits 10 have been opened to openings 15. FIG. 1c is a top view with the expanded intermediate laminate web 16 located in a plane state and with the second material 4a located uppermost.

The expansion may be performed by increasing the velocity of the intermediate laminate web 7 in the machine direction. The more the velocity of the intermediate laminate web 7 is increased, the more the intermediate laminate web 7 is expanded. Thus, the degree of expansion may be modified by regulating the increase of the velocity of the intermediate laminate web 7. The expansion implies that the width of the intermediate laminate web 7 in the transverse direction X is decreased. In the embodiment shown in FIG. 1a, the expansion is performed in the expansion section 14, which is constituted by a lane. The expansion will be further described below.

The dimensions of the produced openings 15 depend on the slit length A of the provided slits 10 in the transverse direction X of the intermediate laminate web 7 and the degree of expansion of the intermediate laminate web 7. In particular embodiments, the intermediate laminate web 7 is expanded to such a degree such that square-shaped openings 15 are formed. However, the intermediate laminate web 7 may be expanded such that openings 15 of any suitable shape are formed.

For example, the opening area of the produced openings 15 of the expanded intermediate laminate web 16 may be 50-2500 mm$^2$, such as 144-400 mm$^2$. In one example, the opening area of the produced openings 15 is about 225 mm$^2$. The term "opening area" is herein intended to denote the area of the opening in an X-Y plane formed by the transverse direction X and the longitudinal direction Y of the expanded intermediate laminate web 16.

Furthermore, a third web 17 of a third material 17a for fixing the expanded intermediate laminate web 16 such that it is maintained in an expanded state is provided into the process and is fed in the direction indicated by the associated arrow. As shown in FIG. 1a, the third web 17 may be provided into the process by being unwound from a third supply roll 18. However, instead of being unwound from a supply roll, the third web 17 may be provided directly from a forming apparatus into the process. The third material will be further described below.

Figure 1D:
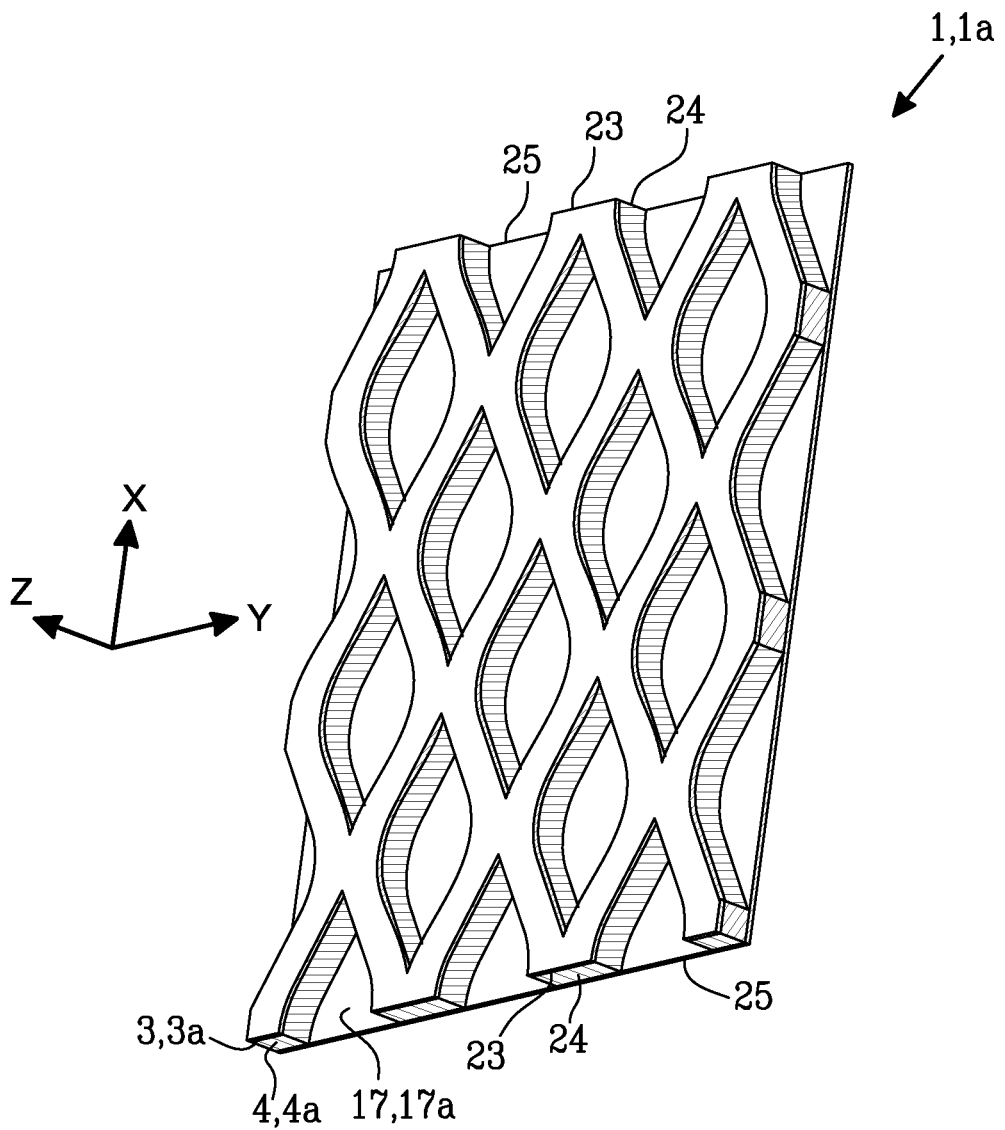
FIG. 1d is a perspective view of a portion of a final laminate material web.

The second material 4a of the expanded intermediate laminate web 16 and the third web 17 are laminated at a second lamination station 20, whereby the expanded intermediate laminate web 16 is fixed in position (i.e. locked) in relation to the third web 17 and is fixed in an expanded state (i.e. with the openings 15 open). This lamination results in that a final laminate material web 1 is formed, which constitutes the web of the laminate material 1a for retaining faeces to be produced by the method according to embodiments of the invention. A portion of the final laminate material web 1 is shown in a perspective view in FIG. 1d. In FIG. 1d the portion of the laminate material web 1 is shown with the first material 3a being located uppermost. The produced laminate material web 1 will be further described below.

In the embodiment shown in FIG. 1a, the lamination of the second material 4a of the expanded intermediate laminate web 16 and the third web 17 is performed by means of a second adhesive, which is applied by means 19a for application of the second adhesive to the second material 4a. More specifically, in the embodiment shown in FIG. 1a, the second adhesive is applied to the second material 4a of the intermediate laminate web 7 before the expansion of the intermediate laminate web 7 and before the provision of the slits 10. In particular embodiments, the second adhesive is applied completely over the surface of the second material 4a of the intermediate laminate web 7. Thereby, the knives 13 of the knife roll 12a utilized for providing the slits 10 need to be forced through the second adhesive as well as the intermediate laminate web 7 in order to provide the slits 10. Thus, the produced film of second adhesive on the surface of the second material 4a is slitted when the transversal slits 10 are provided. Accordingly, no fibers of second adhesive will be formed that bridge over the formed openings 15 after the expansion of the intermediate laminate web 7. Fibers bridging over the formed openings 15 might be sensed against the skin of a user when the produced laminate material 1a is included in an absorbent article for retaining faeces. The second adhesive may be any suitable adhesive for laminating the second material 4a of the expanded intermediate laminate web 16 and the third web 17. For example, the second adhesive may be a hot melt adhesive, a water-based adhesive or a solvent-based adhesive. Examples of adhesives to be utilized as the second adhesive are Dispomelt 2000 (Henkel), NW 1212 (HB Fuller) and H 9564 (Bostik).

However, alternatively, the second adhesive may be applied to the second material 4a of the intermediate laminate web 7 before the expansion of the intermediate laminate web 7 but after the provision of the slits 10. This is indicated in FIG. 1a at reference number 19b. Thereby the knives 13 of the knife roll 12a need not be forced through the second adhesive in order to provide the slits 10. However, then the produced film of second adhesive on the surface of the second material 4a is stretched during the subsequent expansion of the intermediate laminate web 7, whereby thin fibers of the second adhesive may be formed that may bridge over the formed openings 15.

In another alternative, the second adhesive is applied to one of the surfaces of the third web 17 instead of the second material 4a of the intermediate laminate web 7. This is indicated in FIG. 1a at reference number 19c. The second adhesive is then applied on the complete surface of the third web 17.

The means 19a for application of the second adhesive may be constituted by any suitable means for application of adhesive, such as, for example, a slotted glue head or spraying means.

As mentioned above, the lamination of the second material 4a of the expanded intermediate laminate web 16 and the third web 17 is performed at a second lamination station 20. In the embodiment shown in FIG. 1a, the second lamination station 20 includes a second lamination roll 21a and a third lamination roll 21b, which rotate according to the associated arrows. The expanded intermediate laminate web 16 and the third web 17 are fed between the second and third lamination rolls 21a, 21b so as to be laminated by means of the second adhesive.

The second lamination station 20 may include the above described second and third lamination rolls 21a, 21b, but may alternatively include any further or alternative means for lamination of the second material 4a of the expanded intermediate laminate web 16 and the third web 17 by means of the second adhesive. For example, the second lamination station 20 may alternatively include a stationary bar or rod. Furthermore, the lamination of the second material 4a of the expanded intermediate laminate web 16 and the third web 17 may, instead of being performed by means of the second adhesive, be performed by means of any other suitable bonding technique, such as, for example, ultrasonic bonding, thermal bonding or flame lamination. In case ultrasonic bonding, thermal bonding or flame lamination is utilized, the application of the second adhesive is of course omitted and the second lamination station 20 includes any suitable means for performing lamination of the second material 4a of the expanded intermediate laminate web 16 and the third web 17 by means of ultrasonic bonding, thermal bonding or flame lamination (not shown).

Ultrasonic bonding may be performed using a rotary ultrasonic horn. Thermal bonding may be conducted by passing the expanded intermediate laminate web 16 and the third web 17 between two heated rollers. The heated rollers may have smooth surfaces causing lamination over the whole width of the webs 16, 17 or may have pins thereon which form intermittent point bonds between the expanded intermediate laminate web 16 and the third web 17. Flame lamination may be performed by passing a flame over one of the webs 16, 17 to heat the surface thereof, which thereby becomes tacky and forms a bond with the other web 16, 17.

As mentioned above, in the embodiment shown in FIG. 1a, the expansion of the intermediate laminate web 7 is performed in the expansion section 14, which is constituted by a lane. More specifically, in the embodiment shown in FIG. 1a the knife roll 12a and the anvil roll 12b have the same velocity as the lane 14. However, the second and third lamination rolls 21a, 21b have a higher velocity than the knife roll 12a, the anvil roll 12b and the lane 14. Furthermore, the lane 14 has such a holding ability that the intermediate laminate web 7 remains on the surface of the lane 14, but may glide along the surface plane without breaking. The holding ability may be achieved by means of, for example, friction properties of the surface of the lane 14 or a vacuum force. In particular embodiments, a vacuum force is utilized in order to hold the intermediate laminate web 7 onto the lane 14. Due to the fact that the second and third rolls 21a, 21b have a higher velocity than the knife roll 12a, the anvil roll 12b and the lane 14 and the fact that the lane 14 has the above mentioned holding ability, the intermediate laminate web 7 is expanded (i.e. stretched) when positioned on the lane 14 such that the openings 15 are formed.

In the embodiment shown in FIG. 1a, the produced laminate material web 1 is wound onto a storage roll 22 for later usage. However, the produced laminate material web 1 may instead be directly used in production of an absorbent article. Examples of immediate usage of the laminate material web 1 are described below.

The first material 3a (i.e. the material of the first web 3) is a material that is suitable for contacting the skin of a user of the absorbent article. Thus, the first material 3a is compliant, soft-feeling and non-irritating to the user's skin. Examples of suitable materials for use as the first material 3a are different types of nonwoven materials, such as spunbond webs, meltblown webs, carded webs, thermobonded webs, through-airbonded webs, etc. The nonwoven materials may be made of, for example, polypropylene, polyethylene, polyester or bicomponent fibres. Also, the first material 3a may be a laminate or a film material. Preferably, but not necessarily, the first material 3a is hydrophobic. The first material 3a may have a basis weight of, for example, 7-45 gsm (grams per square meter), preferably 10-30 gsm. The first material 3a has suitably a basis weight above 7 gsm in order to be compliant and soft against the skin of the user. Materials with a basis weight below 7 gsm are not very soft to touch. Furthermore, the first material 3a has suitably a basis weight below 45 gsm in order to keep the cost level within a reasonable limit. A disadvantage of the known products today is that they might appear too expensive for the users.

The second material 4a (i.e. the material of the second web 4) is a volume-forming material, i.e. it is a material that imparts volume to the produced laminate material 1a for retaining faeces. In other words, it is a material having such a volume that openings may be formed therein which openings may retain a certain volume of faeces. The second material 4a is at least essentially non-absorbing. Examples of suitable materials for use as the second material 4a are foam materials made of e.g. polyurethane. Other examples of suitable materials for use as the second material 4a are bulky fibrous materials, e.g. high loft materials made of, for example, polypropylene, polyethylene, polyester or bicomponent fibres. The second material 4a may have a thickness of, for example, 1-10 mm, preferably 2-4 mm. The second material 4a has suitably a thickness below 10 mm, since a thickness above 10 mm is likely to imply that a reticulated pattern is formed on the user's body corresponding to the reticulated shape of the second material 4a of the laminate material web 1. Furthermore, the second material 4a has suitably a thickness above 1 mm since there might be difficulties in the production process in case the thickness is below 1 mm.

When measuring the thickness of the second material 4a, the following method should be used. A material test sample should be conditioned during at least 24 hours. By conditioned is meant that the sample should be placed on a flat surface and having no pressure exerted on it. The room in which the conditioning takes place should have a temperature of 23° C. and a relative humidity of 50%. After conditioning, the thickness of the material is measured with a thickness gauge. The gauge has a square foot with dimensions 50×50 mm (i.e. having an area of 25 $cm^2$) and exerts a pressure of 0.5 kPa. The foot should be lowered slowly and carefully. The thickness is read when the foot has rested over the material for 10 seconds.

The third material 17a (i.e. the material of the third web 17) is a material that is suitable for fixing the expanded intermediate laminate web 16 such that it is maintained in an expanded state, i.e. it is a material that implies that the expanded intermediate laminate web 16 is maintained such that the openings 15 are opened when the expanded intermediate laminate web 16 is laminated to the third material 17a. Examples of suitable materials for use as the first material 1a are different types of nonwoven materials, such as spunbond webs, meltblown webs, carded webs, thermobonded webs, through-air-bonded webs, etc. The nonwoven materials may be made of, for example, polypropylene, polyethylene, polyester or bicomponent fibres. Also, the first material 1a may be a laminate or a film material. Preferably, but not necessarily, the first material 1a is hydrophilic. The third material 17a may have a basis weight of, for example, 10-30 gsm (grams per square meter), preferably 15-25 gsm. The third material 17a has suitably a basis weight above 10 gsm, since a third material 17a with a basis weight below 10 gsm would imply that there is a risk that it causes SAP (superabsorbent polymer) particles to escape from the absorbent core. This is especially relevant when the laminate material 1a of the laminate material web 1 is utilized in embodiments of absorbent articles in which there is no topsheet present over the whole core surface and the laminate material 1a acts as a topsheet. Such embodiments will be further described below. Furthermore, in case the third material 17a would have a basis weight above 30 gsm, there would be a risk that the liquid acquisition into the absorbent core is impaired by the third material 17a.

As shown in FIG. 1d, the first material 3a of the produced laminate material web 1 includes two longitudinal first material edges 23, the second material 4a of the produced laminate material web 1 includes two longitudinal second material edges 24 and the third material 17a of the produced laminate material web 1 includes two third material edges 25. The term "material edge" refers herein to an outer edge of a material which delimits the material in an X-Y plane, which is formed by the transverse direction X and the longitudinal direction Y of the material, when the material is positioned in a plane state. A material edge includes outermost points of the material along a straight line. Thus, the material is not necessarily continuous in a material edge, but may be non-continuous and include the outermost parts of ends of the material. However, the material may also be continuous in the material edge. In other words, the material may be non-continuous or continuous along the straight line along which the material edge extends.

In accordance with the above definition, each longitudinal first material edge 23 of the web 1 shown in FIG. 1d includes the outermost points of the first material 3a along a straight line extending in the longitudinal direction Y, i.e. it includes borders of the first material 3a not being positioned within any of the openings 15 (FIG. 1d). The first material 3a of the web 1 shown in FIG. 1d is non-continuous in the longitudinal first material edges 23. Likewise, each longitudinal second material edge 24 of the web 1 shown in FIG. 1d includes the outermost points of the second material 4a along a straight line extending in the longitudinal direction Y, i.e. it includes borders of the second material 4a not being positioned within any of the openings 15. The second material 4a of the web 1 shown in FIG. 1d is non-continuous in the longitudinal second material edges 24. However, the third material 17a of the web 1 shown in FIG. 1d is continuous in the longitudinal third material edges 25.

As shown in FIG. 1d, the laminate material web 1 may be produced such that the third material 17a of the laminate material web 1 does not extend outside the longitudinal first material edges 23 and the longitudinal second material edges 24 of the web 1.

Figure 1E:
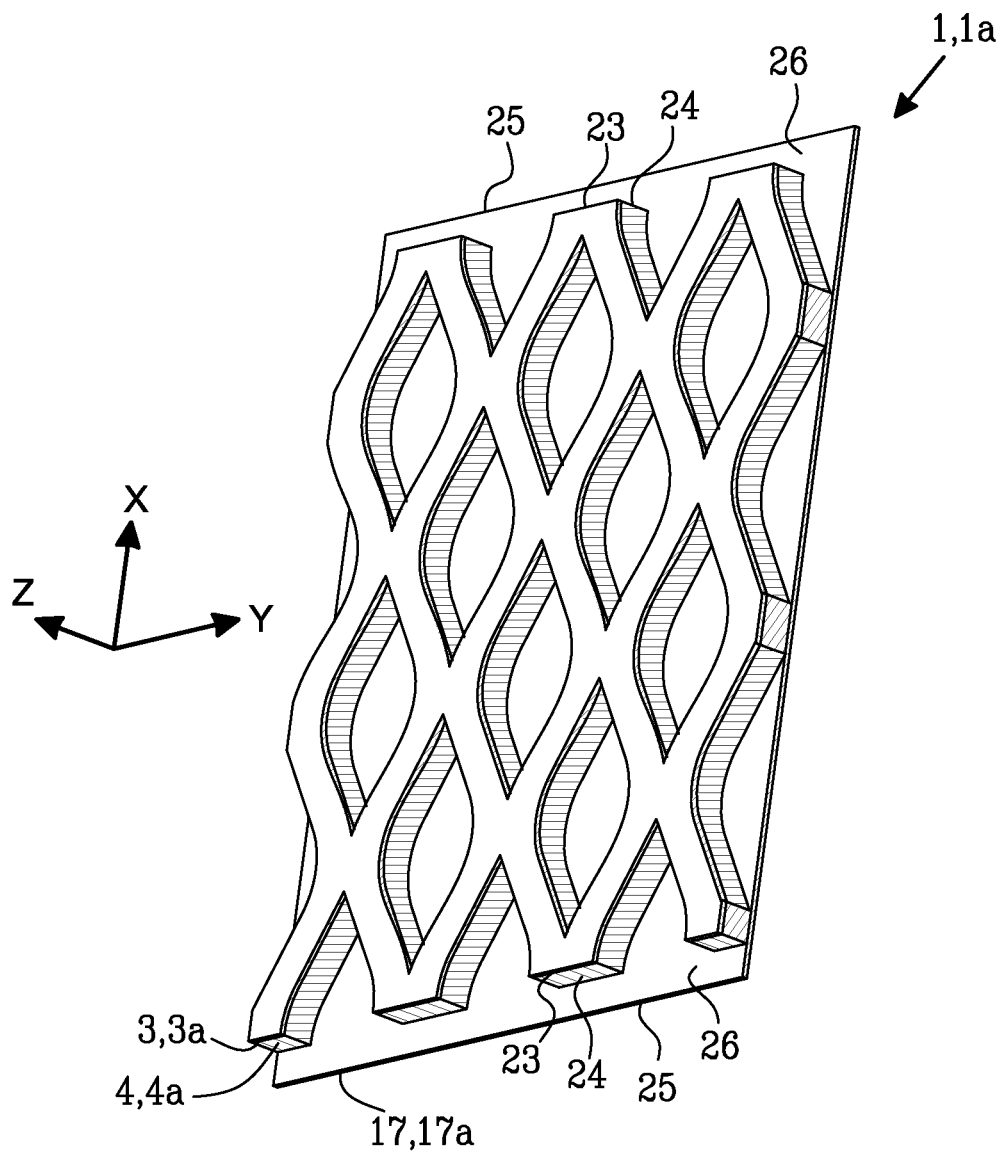
FIG. 1e is a perspective view of a portion of a variant of the final laminate material web.

However, alternatively the laminate material web 1 may be produced such that the third material 17a of the laminate material web 1 extends outside the longitudinal first material edges 23 and the longitudinal second material edges 24 in the transverse direction X (FIG. 1e). Thus, the third material 17a has then a greater width in the transverse direction X than the first and second materials 3a, 4a of the laminate material web 1 and the third material 17a of the laminate material web 1 includes two longitudinal portions of non-laminated third material 26. The term "longitudinal portion of non-laminated third material" is herein intended to denote a portion of the third material 17a which extends in the longitudinal direction Y and in which the third material 17a is non-laminated to the second material 4a. Optionally, the non-laminated third material 26 may be folded and bonded to the first material 3a so as to cover at least the longitudinal first material edges 23 and the longitudinal second material edges 24 of the laminate material web 1 by the non-laminated third material 26 (FIG. 10. The folding and bonding (not shown in FIG. 1a) may be performed before or after the produced laminate material web 1 is wound onto the storage roll 22. In case the laminate material web 1 is directly used in production of an absorbent article, the folding and bonding are performed before the laminate material web 1 is cut into pieces. This will be further described below.

The laminate material 1a produced by the above described method is especially effective in handling and retaining low-viscosity fecal material, which is prevalent in younger children especially those who are breast fed, and also in users having diarrhea. Such low-viscosity fecal material easily moves around on the body facing side of the topsheet and increases the risk for leakage, and further smears it against the skin of the user making cleanup more difficult. By including the laminate material 1a in an absorbent article in association with the topsheet in at least a fecal receiving area such that a plurality of openings 15 are exposed to the user, improved immobilization of low-viscosity fecal material is obtained. The fecal receiving area is the area that immediately surrounds the point of the absorbent article 2 that is positioned opposite to the user's anus.

The fact that the second material 4a is a volume forming material in accordance with the above described implies that the openings 15 have a certain depth in the thickness direction Z. Low-viscosity fecal material (as well as more solid forms of fecal material) may move into the exposed openings 15, which together with the third material 17a covering the openings 15 on the garment facing side form containment wells. Fecal material comprised within the openings 15 is spaced apart from the user's skin, whereby smearing of fecal material against the skin of the user is reduced. In addition, fecal material comprised within the openings 15 is inhibited from moving around on the topsheet. Thus, the openings 15 imply that the immobilization of fecal material (i.e. the retaining of fecal material) is improved and that the risk of leakage of fecal material is reduced. Accordingly, the laminate material 1a with the openings 15 is suitable to utilize in an absorbent article for retaining faeces.

Furthermore, the above described method for producing the web 1 of the laminate material 1a for retaining faeces may result in no waste of the first, second and third materials 3a, 4a, 17a during production since no parts need to be punched or cut from any of the materials 3a, 4a, 17a in order to form the web 1. Thus, handling of waste material is reduced. A further advantage is that the expansion of the intermediate laminate web 7 may easily be changed, thereby altering the size and shape of the openings 15 of the produced expanded laminated web 16. Also, the expanded intermediate laminate web 16 is locked in an expanded state, i.e. the laminate web of the first material 3*a* and the second material 4*a* is locked such that it has an open structure in which the openings 15 are opened, by means of the third material web 17. This implies that the first material 3*a* and the second material 4*a* may be stored in an open structure on a roll and used at a later stage. The fact that the laminate web of the first material 3*a* and the second material 4*a* is locked in an open state implies also that already existing machines for producing absorbent articles need not be altered so much in order to incorporate a piece comprising the first material 3*a* and the second material 4*a* in an open state in an absorbent article. In case the laminate web of the first material 3*a* and the second material 4*a* would not be locked in an open state, existing machines for producing absorbent articles would have to be substantially altered in order to enable expansion of the laminate web of the first material 3*a* and the second material 4*a* into an open state and in order to enable that the open state is maintained when applying a piece thereof in an absorbent article.

The above described method for producing the web 1 of the laminate material 1*a* for retaining faeces may be included in a method for producing an absorbent article. Thus, the present disclosure relates also to a method for producing an absorbent article, which includes a step of producing the web 1 of the laminate material 1*a* for retaining faeces according to any of the above described embodiments of the method for producing the web 1 of the laminate material 1*a* or any described alternatives or variants thereof. In an embodiment of the method for producing an absorbent article, the produced web 1 of the laminate material 1*a* may be directly utilized for application to other parts of an absorbent article after production. However, the method for producing an absorbent article may alternatively include storing the produced web 1 of the laminate material 1*a* on a storage roll and later utilizing the web 1 for application to other parts of an absorbent article. The method for producing an absorbent article will be further described in the following.

Figure 2A:
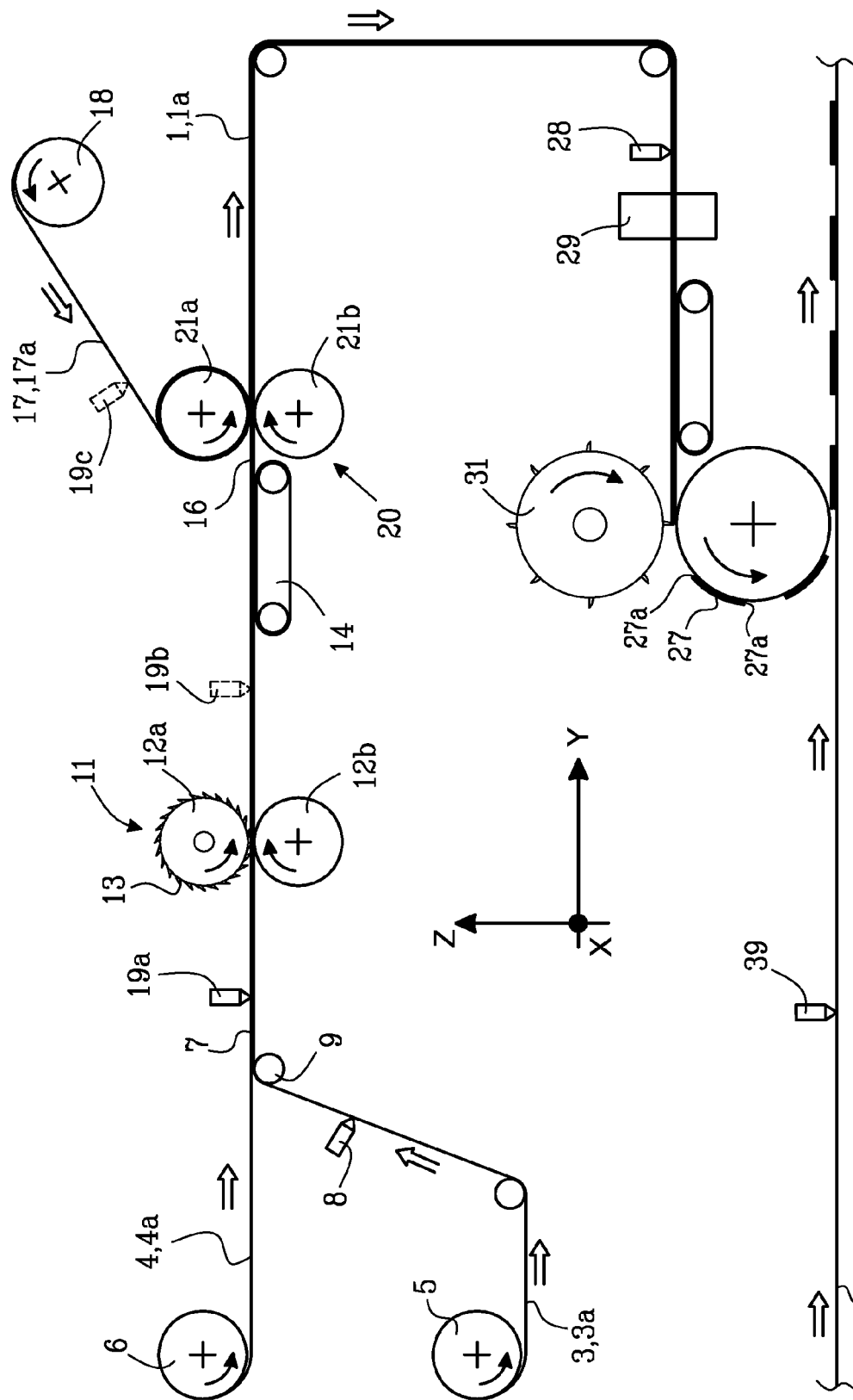
FIG. 2a illustrates schematically a first embodiment of the method for producing an absorbent article according to the invention.

FIG. 2*a* illustrates schematically a first embodiment of the method for producing an absorbent article. The first embodiment includes a step of producing the web 1 of the laminate material 1*a* by means of the method for producing the web 1 of the laminate material 1*a* described above in connection with FIG. 1*a*. FIG. 2*a* corresponds to FIG. 1*a* with the exception that in FIG. 2*a* the produced web 1 is directly utilized for application to other parts of an absorbent article instead of being wound onto a storage roll for later usage. The description of parts of FIG. 2*a* that correspond to FIG. 1*a* are not repeated, but reference is made to the above description. The method in the step for producing the web 1 of the laminate material 1*a* of the first embodiment may be varied in accordance with the variants described in connection with FIG. 1*a*.

In the embodiment shown in FIG. 2*a*, the produced web 1 of the laminate material 1*a* is directly utilized for application to other parts of an absorbent article 2. Furthermore, in the embodiment shown in FIG. 2*a*, the final laminate material web 1 is produced such that the third material 17*a* extends outside the longitudinal first material edges 23 and the longitudinal second material edges 24 in accordance with FIG. 1*e*. Thus, the first material 3*a* of the produced laminate material web 1 includes two longitudinal first material edges 23 and the second material 4*a* of the produced laminate material web 1 includes two longitudinal second material edges 24. The third material 17*a* of the produced laminate material web 1 extends outside the longitudinal first material edges 23 and the longitudinal second material edges 24 such that the third material 17*a* of the laminate material web 1 includes two longitudinal portions of non-laminated third material 26 in accordance with the description in conjunction with FIG. 1*e*.

Figure 1F:
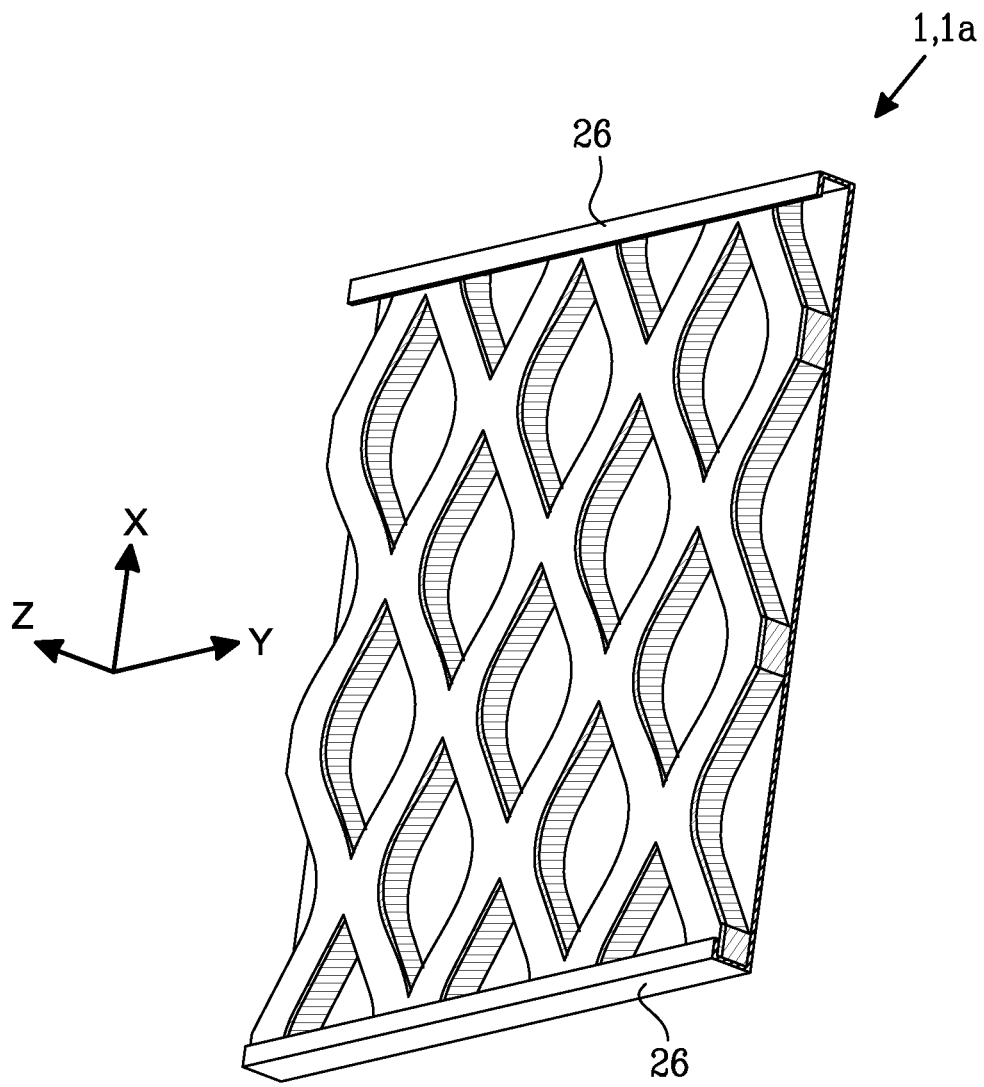
FIG. 1f is a perspective view of a portion of the laminate material web shown in FIG. 1e with non-laminated third material folded and bonded to a first material of the web.

Furthermore, in the embodiment shown in FIG. 2*a*, the method for producing the laminate material web 1 includes further a step of folding and bonding the non-laminated third material 26 of the produced laminate material web 1 to the first material 3*a* so as to cover at least the longitudinal first material edges 23 and the longitudinal second material edges 24 of the web 1 by the non-laminated third material 26. As shown in FIG. 2*a*, the step of folding and bonding may, for example, be performed by applying a third adhesive to any of the first material 3*a* and the non-laminated third material 26 of the laminate material web 1 by means 28 for application of adhesive, after which the non-laminated third material 26 is folded and bonded to the first material 3*a* by means of the third adhesive. The means 28 for application of third adhesive may be, for example, a slotted glue head or spraying means. However, alternatively any suitable means for application of the third adhesive may be utilized. For example, the third adhesive may be a hot melt adhesive, a water-based adhesive or a solvent-based adhesive. Examples of adhesives to be utilized as the third adhesive are Dispomelt 2000 (Henkel), NW 1212 (HB Fuller) and H 9564 (Bostik). As shown in FIG. 2*a*, the folding and bonding may be performed by means of a folding and bonding unit 29. Alternatively, any other suitable means may be utilized for the folding and bonding. Alternatively, the bonding may be performed by means of ultrasonic bonding, thermal bonding or mechanical bonding instead of by means of the third adhesive. FIG. 1*f* shows a portion of the laminate material web 1 after the step of folding and bonding the laminate material web 1 shown in FIG. 1*e*.

Figure 2B:
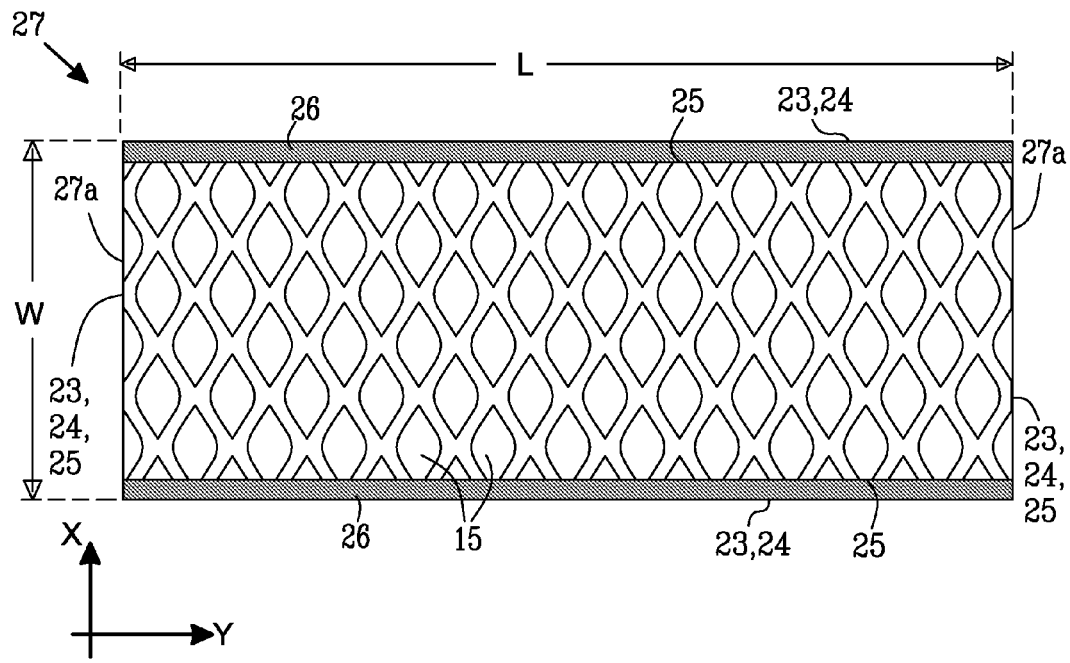
FIG. 2b is a top view of a laminate material piece produced in the first embodiment with the first material located uppermost.

After folding and bonding the non-laminated third material 26 to the first material 3*a* of the laminate material web 1, a piece 27 of the web 1 is produced as shown in FIG. 2*a*. In the first embodiment, the laminate material piece 27 is produced by cutting through the thickness of the final laminate web 1 in the thickness direction Z along two transverse cutting lines 27*a*, i.e. two cutting lines extending in the transverse direction X of the web 1. FIG. 2*b* is a top view of the produced laminate material piece 27 with the first material 3*a* located uppermost. The laminate material piece 27 is produced such that it includes a plurality of the openings 15 comprised in the web 1, i.e. the produced laminate material piece 27 has such a width W in the transverse direction X and length L in the longitudinal direction Y, respectively, when positioned in a plane state that it comprises a plurality of openings 15. In FIG. 2*b* the cutting lines are straight, but may have any suitable shape.

Figure 2C:
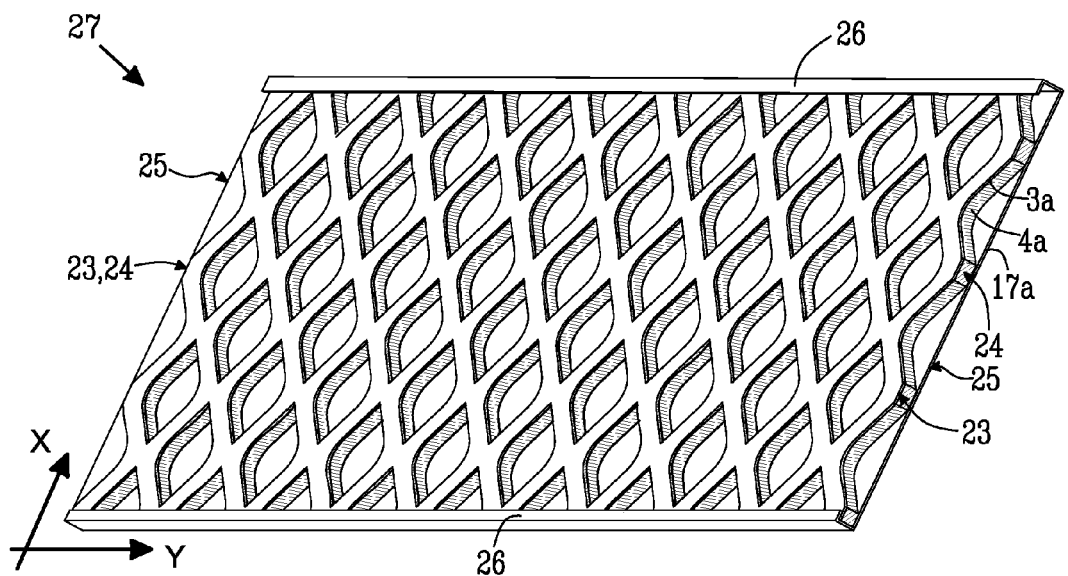
FIG. 2c is a perspective view of the laminate material piece shown in FIG. 2b.

FIG. 2*c* is a perspective view of the produced laminate piece 27 shown in FIG. 2*b* with the first material 3*a* located uppermost. As shown in FIG. 2*c*, the first material 3*a* of the laminate material piece 27 has first material edges 23, the second material 4*a* of the laminate material piece 27 has second material edges 24 and the third material of the laminate material piece 27 has third material edges 25. As mentioned above, the term "material edge" refers herein to an outer edge of a material which delimits the material in an X-Y plane, which is formed by the transverse direction X and the longitudinal direction Y of the material, when the material is positioned in a plane state. A material edge includes outermost points of the material along a straight line. Thus, the material is not necessarily continuous in a material edge, but may be non-continuous and include the outermost parts of ends of the material. However, the material may also be continuous in the material edge.

More specifically, the first material 3a of the laminate material piece 27 shown in FIG. 2c includes two longitudinal first material edges 23 and two transversal first material edges 23. Each longitudinal first material edge 23 includes the outermost points of the first material 3a along a straight line extending in the longitudinal direction Y, i.e. it includes borders of the first material 3a not being positioned within any of the openings 15. Each transversal first material edge 23 includes the outermost points of the first material 3a along a straight line extending in the transverse direction X, i.e. it includes borders of the first material 3a not being positioned within any of the openings 15. Thus, the first material 3a is non-continuous in the first material edges 23 in FIG. 2c. Likewise, the second material 4a of the laminate material piece 27 shown in FIG. 2c includes two longitudinal second material edges 24 and two transversal second material edges 24. The third material 17a of the laminate material piece 27 shown in FIG. 2c includes two longitudinal third material edges 25 and two transversal third material edges 25. However, the third material 17a is continuous in the third material edges 25. The longitudinal first material edges 23 and the longitudinal second material edges 24 are covered by the non-laminated third material 26.

In the embodiment shown in FIG. 2a, the laminate material piece 27 is produced by cutting a piece from the final laminate web 1 by means of a rotary cutting knife 31. However, any suitable means for producing the laminate material piece 27 may be utilized.

Figure 2D:
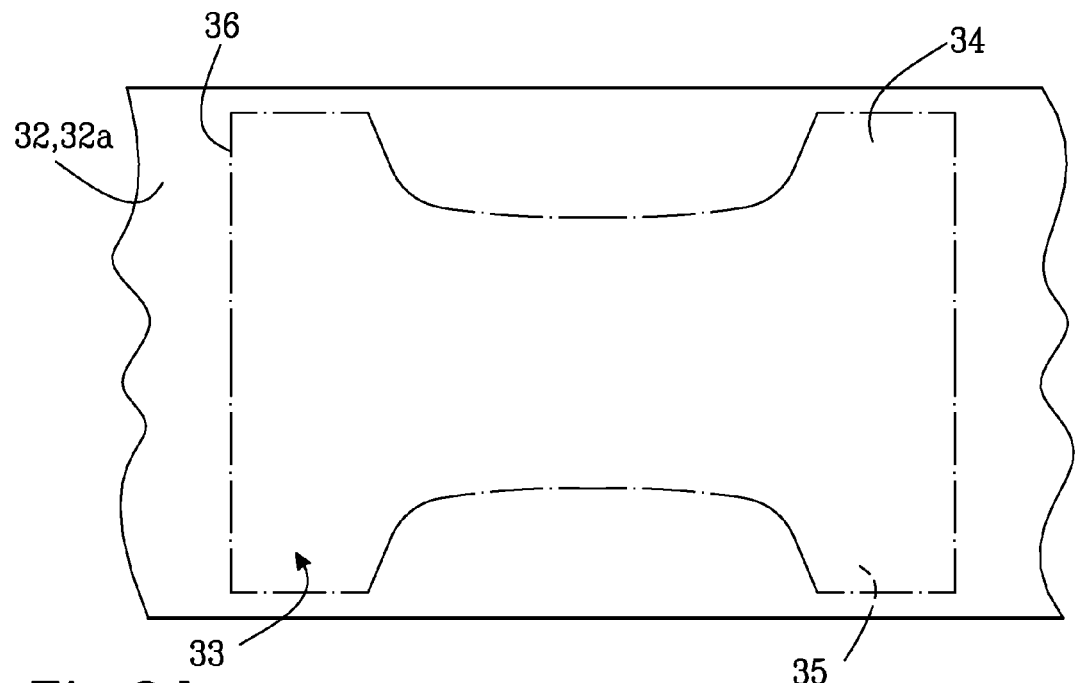
FIG. 2d shows a top view of a portion of a web of a topsheet material.

Furthermore, in the first embodiment of the method for producing an absorbent article, a liquid permeable topsheet 33 for the absorbent article 2 is provided. More specifically, in the first embodiment shown in FIG. 2a, a web 32 of a liquid permeable topsheet material 32a is provided and the topsheet 33 is produced from the web 32. The borders 36 delimiting the topsheet 33, i.e. the shape of the topsheet 33, to be produced of the topsheet material 32a is indicated by dashed lines in FIG. 2d, which shows a top view of a portion of the web 32 of the topsheet material 32a. The topsheet 33 has a first surface 34 arranged to face a user of the absorbent article and a second surface 35 arranged to face away from the user of the absorbent article. According to the first embodiment of the method for producing an absorbent article, the topsheet 33 is cut from the web 32 along cutting lines corresponding to the dashed lines shown in FIG. 2d in a step later in the process. However, the topsheet 33 may be cut from the web 32 at any suitable point in the process. Also, the topsheet 33 may be provided as a discrete piece, i.e. not included in a continuous web, (not shown) into the process.

Figure 2E:
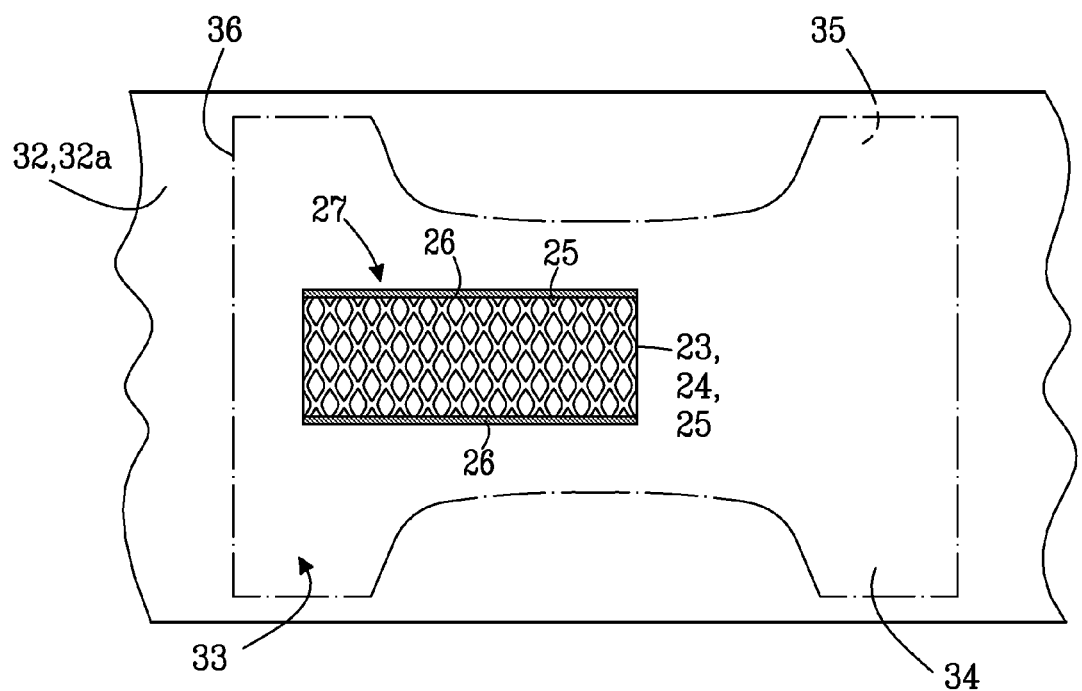
FIG. 2e shows the portion of the web shown in FIG. 2d after application of the laminate material piece shown in FIG. 2b.

In the first embodiment, the produced laminate material piece 27 is applied to the first surface 34 of the topsheet 33, whereby the laminate material piece 27 is applied to the first surface 34 such that the first material 3a is arranged to face the user and such that a plurality of the openings 15 of the laminate material piece 27 not being covered by the non-laminated third material 26 are arranged to be exposed to the user. FIG. 2e shows a portion of the web 32 after application of the laminate material piece 27 seen from a user-facing side of the topsheet 33, i.e. with the first surface 34 of the web 32 being located uppermost.

More specifically, in the first embodiment the laminate material piece 27 is produced to have such a size and shape and is applied to the first surface 34 of the topsheet 33 such that it extends within the borders 36 of the topsheet 33 (i.e. it does not extend outside the borders 36 after application to the topsheet 33). The laminate material piece 27 is sized and applied such that it is at least positioned in that part of the produced absorbent article that constitutes the fecal receiving area, which is the area that immediately surrounds the point of the absorbent article that is positioned opposite to the user's anus.

In the embodiment shown in FIG. 2a, the laminate material piece 27 is bonded to the topsheet 33 (FIGS. 2d-e) by means of a fourth adhesive. The fourth adhesive is applied to the first surface 34 of the topsheet 33 by means 39 for application of adhesive before the laminate material piece 27 is applied to the topsheet 33. The means 39 for application of fourth adhesive may be, for example, a slotted glue head or spraying means. However, alternatively any suitable means for application of the fourth adhesive to the topsheet 33 may be utilized. Also, the fourth adhesive may instead be applied to the laminate material piece 27. For example, the fourth adhesive may be a hot melt adhesive, a water-based adhesive or a solvent-based adhesive. Examples of adhesives to be utilized as the fourth adhesive are Dispomelt 2000 (Henkel), NW 1212 (HB Fuller) and H 9564 (Bostik).

Figure 2F:
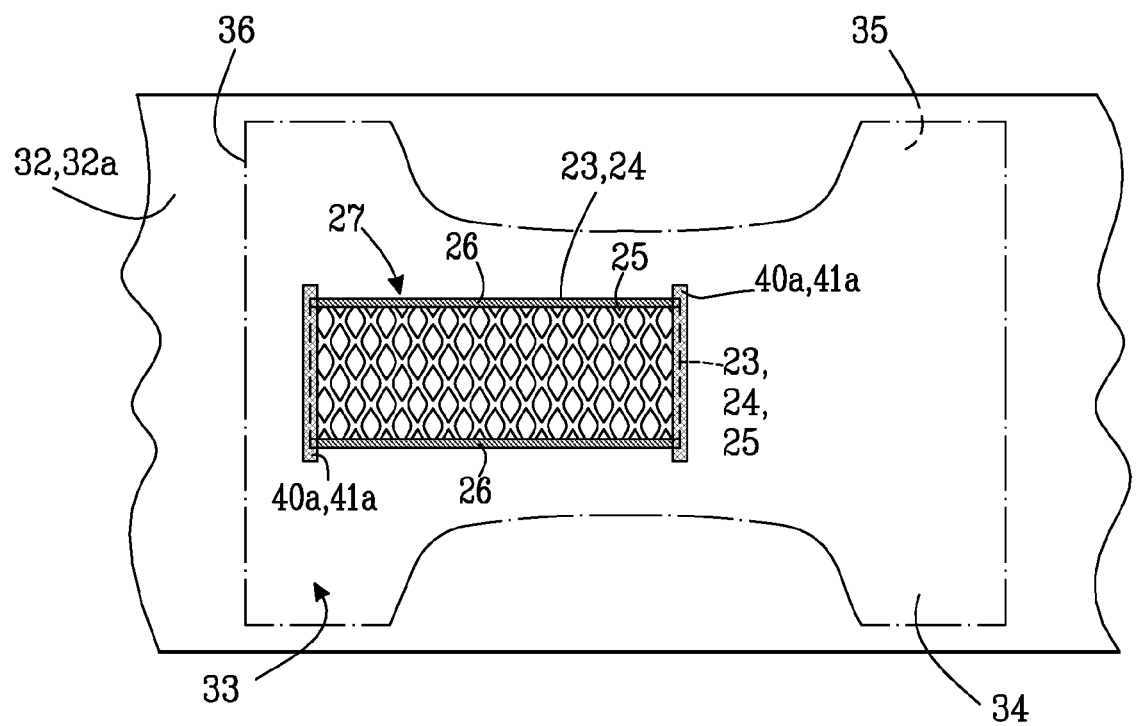
FIG. 2f shows the portion of the web shown in FIG. 2e after application of a first edge cover arrangement.

Furthermore, in the first embodiment a first edge cover arrangement 40a including two first edge cover pieces 41a of an edge cover material is provided. In the first embodiment each first edge cover piece 41a is applied such that all first material edges 23 and all second material edges 24 of the laminate material piece 27 are covered by a combination of the folded and bonded non-laminated third material 26 and the first edge cover arrangement 40a and are arranged to be non-exposed to (i.e. concealed for) said user (FIG. 2f). The non-exposure of the first material edges 23 and the second material edges 24 to the user implies that the risk that material parts of those edges are ripped up due to contact with the skin of the user is avoided. FIG. 2f shows a top view of a portion of the web 32 of topsheet material 32a after application of the produced laminate material piece 27 shown in FIG. 2b and after application of the first edge cover arrangement 40a.

More specifically, in the first embodiment each first edge cover piece 41a is applied such that it is partly positioned adjacently over the laminate material piece 27 and partly positioned adjacently over the topsheet 33. The expression "partly positioned adjacently over" is herein intended to mean that parts of a component is positioned adjacently over (i.e. on) another component when seen from a user facing side. In addition, each first edge cover piece 41a is sized and positioned such that all first material edges 23 and all second material edges 24 are covered by a combination of the non-laminated third material 26 and the first edge cover arrangement 40a. The first edge cover pieces 41a cover also the transverse third material edges 25. As shown in FIG. 2f, the first edge cover pieces 41a may be strip-shaped. As also shown in FIG. 2f, the first edge cover pieces 41a may overlap the non-laminated third material 26 in certain areas.

Furthermore, in the first embodiment the first edge cover pieces 41a are bonded to the first material 3a of the laminate material piece 27, the non-laminated third material 26 (in corners) and the topsheet 33. However, instead of being bonded to the topsheet 33, the first edge cover pieces 41a may be bonded to any other suitable component of the produced absorbent article positioned outside the first, second and third material edges 23, 24, 25. The first edge cover pieces 41a may be bonded to the laminate material piece 27 and to the topsheet 33 or any other components by means of any suitable adhesive or by means of heat bonding, ultrasonic bonding or mechanical bonding.

The first embodiment of the method for producing an absorbent article may be varied in that the first edge cover arrangement 40a includes any other suitable number of first edge cover pieces 41a than two. However, in all variants of the first embodiment, the first edge cover arrangement 40a includes at least two first edge cover pieces 41a and each first edge cover piece 41a is applied such that all first material edges 23 and all second material edges 24 of the laminate material piece 27 are covered by a combination of the non-laminated third material 26 and the first edge cover arrangement 40a and are arranged to be non-exposed to the user.

A second embodiment of the method for producing an absorbent article corresponds to the first embodiment shown in FIG. 2a except for concerning the fact that the laminate material web 1 is produced in the second embodiment such that the third material 17a does not extend outside the longitudinal first material edges 23 and the longitudinal second material edges 24 of the laminate material web 1 (FIG. 1d). Thus, the step of folding and bonding non-laminated third material 26 in the first embodiment is omitted in the second embodiment. In addition, a second edge cover arrangement 40b (FIG. 3d) is utilized in the second embodiment instead of the first edge cover arrangement 40a utilized in the first embodiment.

Figure 3A:
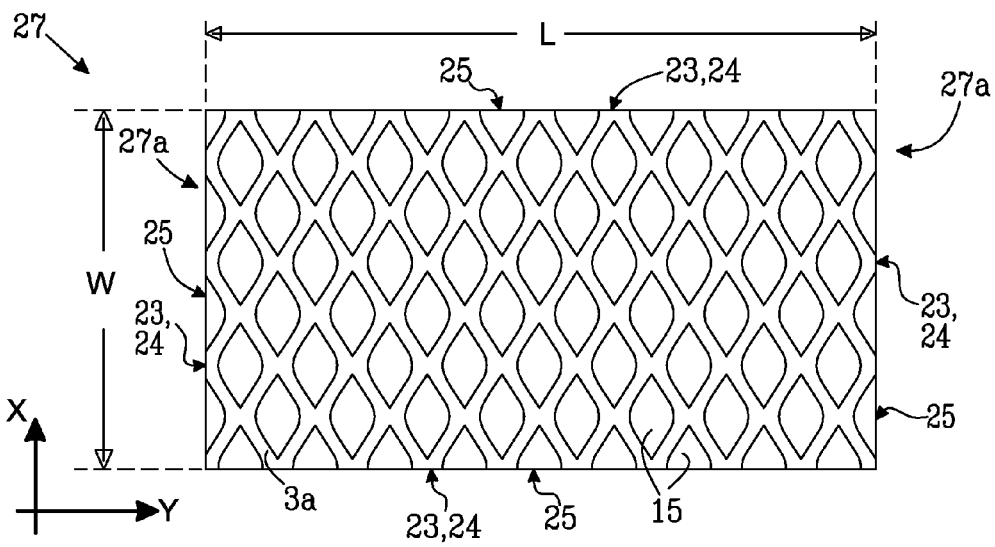
FIG. 3a is a top view of a laminate material piece produced in the second embodiment with the first material located uppermost.
Figure 3B:
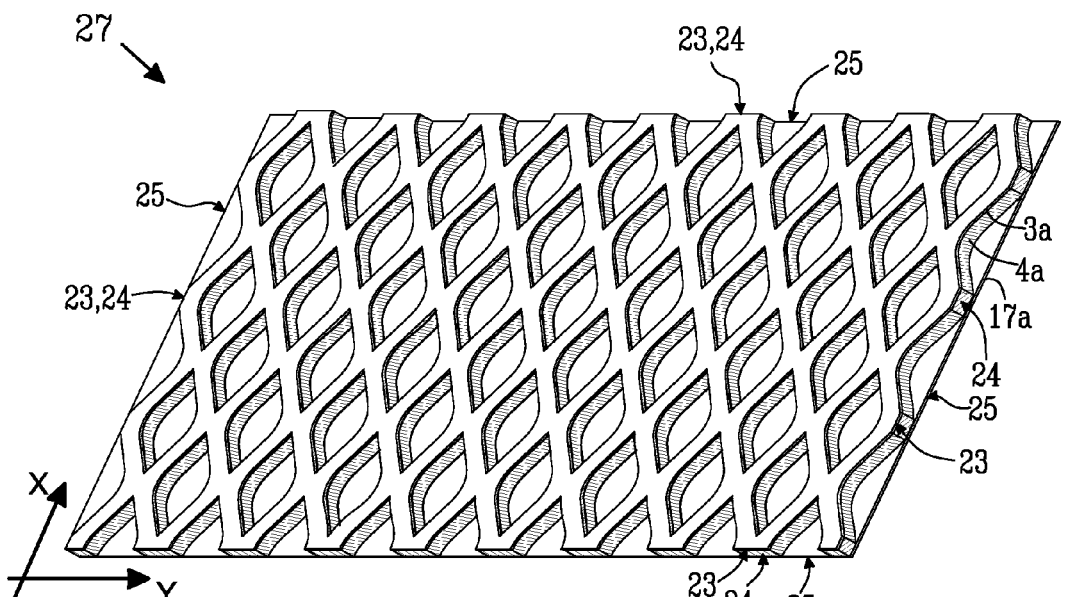

In accordance with the first embodiment, a piece of the laminate material web 1 is produced by cutting through the thickness of the laminate material web 1 in the thickness direction Z along two transverse cutting lines 27a in the second embodiment. However, the third material 17a of the laminate material piece 27 produced by means of the cutting along the two transverse cutting lines 27a in the second embodiment does not extend outside the longitudinal first material edges 23 and the longitudinal second material edges 24 of the produced laminate material piece 27. FIGS. 3a and 3b show a top view and a perspective view, respectively, of the laminate material piece 27 produced in accordance with the second embodiment, whereby the first material 3a is located uppermost. The laminate material piece 27 is produced such that it includes a plurality of the openings 15 comprised in the web 1, i.e. the produced laminate material piece 27 has such a width W in the transverse direction X and length L in the longitudinal direction Y, respectively, when positioned in a plane state that it includes a plurality of openings 15. In FIGS. 3a-b the cutting lines are straight, but may have any suitable shape. As may be seen in FIGS. 3a-b, the laminate material piece 27 produced in accordance with the second embodiment includes two longitudinal first material edges 23, two transverse first material edges 23, two longitudinal second material edges 24, two transverse second material edges 24, two longitudinal third material edges 25 and two transverse third material edges 25.

Furthermore, in the second embodiment the produced laminate material piece 27 is applied to the first surface 34 of the topsheet 33 such that the first material 3a of the laminate material piece 27 is arranged to face the user and the third material 17a is arranged to be in contact with the topsheet 33. In addition, the laminate material piece 27 is produced such that it has such a size and shape and is applied to the topsheet 33 such that it extends within the borders 36 of the topsheet 33 (i.e. it does not extend outside the borders 36 after application to the topsheet 33). The laminate material piece 27 is applied such that it is at least positioned in that part of the produced absorbent article that constitutes the fecal receiving area.

Figure 3C:
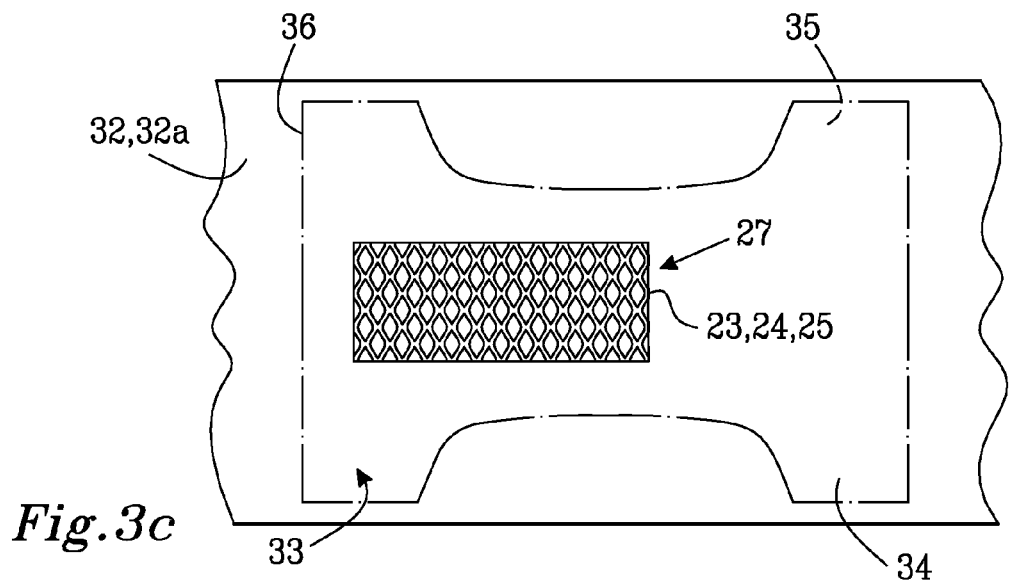

FIG. 3c shows a portion of the web 32 of the topsheet material 32a after application of the laminate material piece 27 to the first surface 34 of the topsheet 33 according to the second embodiment. The laminate material piece 27 may be bonded to the first surface 34 by means of the fourth adhesive or any of the other bonding techniques as described in connection with the first embodiment.

Figure 3D:
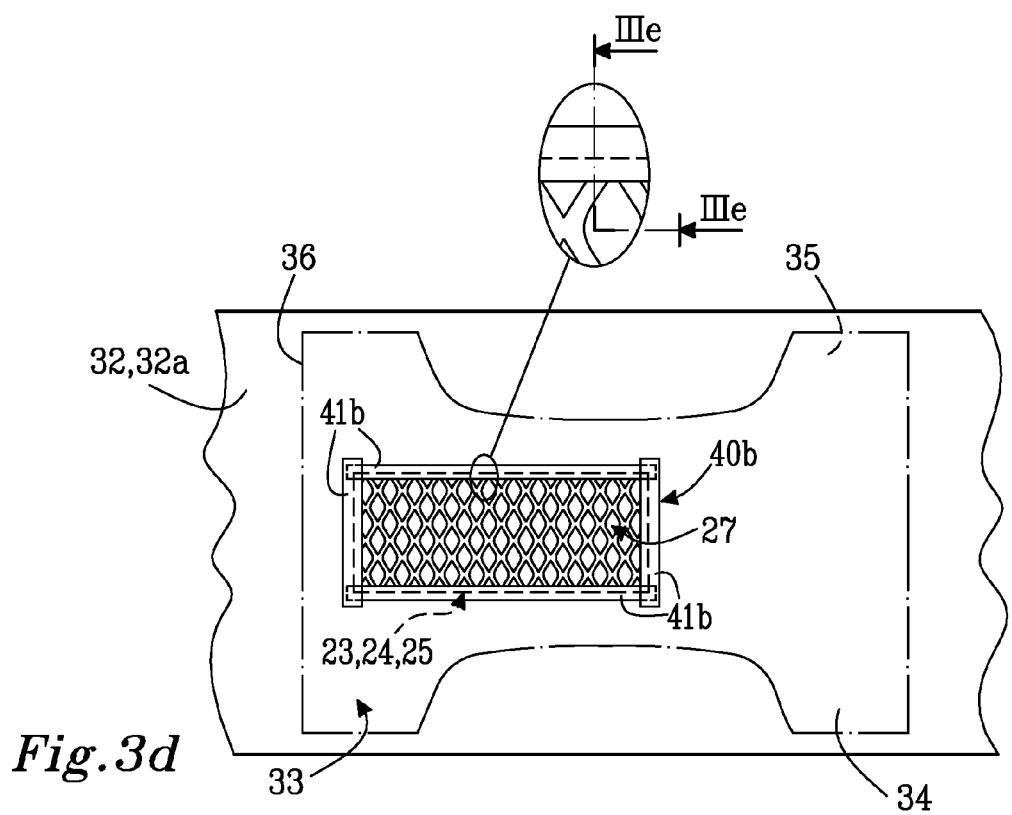
FIG. 3d shows the portion of the web shown in FIG. 3c after application of a second edge cover arrangement.
Figure 3E:
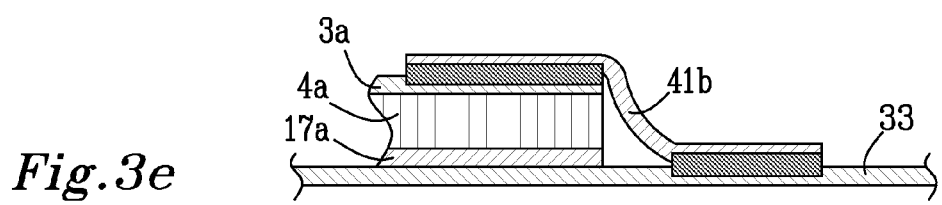
FIG. 3e is a cross-sectional view according to line IIIe-IIIe in FIG. 3d.

Furthermore, in the second embodiment of the method for producing an absorbent article a second edge cover arrangement 40b including four first edge cover pieces 41b of an edge cover material is provided (FIGS. 3d-e). The edge cover material will be further described below.

In the second embodiment each second edge cover piece 41b is applied such that all first material edges 23, all second material edges 24 and all third material edges 25 of the laminate material piece 27 are covered by the second edge cover arrangement 40b and are arranged to be non-exposed to the user. Each second edge cover piece 41b is applied such that it is partly positioned adjacently over the laminate material piece 27 and partly positioned adjacently over the topsheet 33 (FIGS. 3d-e). Thus, each second edge cover piece 41b is sized and positioned such that all first material edges 23, all second material edges 24 and all third material edges 25 of the laminate material piece 27 are covered by the second edge cover arrangement 40b and are arranged to be non-exposed to the user. Accordingly, the second edge cover pieces 41b of the second edge cover arrangement 40b cover together the first, second and third material edges 23, 24, 25 of the laminate material piece 27 after application so as to avoid contact thereof with the user.

FIG. 3d shows a top view of the portion of the web 32 shown in FIG. 3c after application of the second edge cover arrangement 40b. FIG. 3e is a cross-sectional view according to line IIIe-IIIe in FIG. 3d. As shown in FIG. 3d the second edge cover pieces 41b may be strip-shaped. As also shown in FIG. 3d the second edge cover pieces 41b may overlap each other in certain areas.

The second embodiment of the method for producing an absorbent article may be varied in that the second edge cover arrangement 40b includes any other suitable number of second edge cover pieces 41b than four. In addition, the second embodiment may be varied in that the laminate material web 1 is produced such that the third material 17a extends outside the longitudinal first material edges 23 and the longitudinal second material edges 24 of the laminate material web 1 such that the web 1 includes two longitudinal portions of non-laminated third material 26 (FIG. 1e). In the variants of the second embodiment, the non-laminated third material 26 is not folded and bonded to the first material 3a as in the first embodiment. Thus, the third material 17a of the laminate material piece 27 produced by means of the cutting along the two transverse cutting lines 27a extends then outside the longitudinal first material edges 23 and the longitudinal second material edges 24 of the produced laminate material piece 27 (not shown). The second edge cover arrangement 40b may then be produced and applied such that all first, second and third material edges 23, 24, 25 of the laminate material piece 27 are covered by the second edge cover arrangement 40b or such that only the first and second material edges 23, 24 are covered by the second edge cover arrangement 40b.

Furthermore, in FIGS. 3a-d the produced laminate material piece 27 has a rectangular shape. However, the produced laminate material piece 27 may have any suitable shape, such as, for example, oval, heart-shaped or square-shaped. Depending on, for example, the shape of the laminate material piece to produce, the laminate material piece may be produced by cutting through the thickness of the laminate material web 1 in the thickness direction Z along one or more cutting lines, which may have any suitable shape. In case the laminate material piece 27 is produced to have another shape than that shown in FIGS. 3a-d, it may have other numbers of first material edges, second material edges and third material edges than those specified above for the laminate material piece 27 shown in FIGS. 3*a*-*d*.

In all variants of the second embodiment, the second edge cover arrangement 40*b* includes at least one second edge cover piece 41*b* and each second edge cover piece 41*b* is applied such that at least all first material edges 23 and all second material edges 24 of the laminate material piece 27 are covered by the second edge cover arrangement 40*b* and arranged to be non-exposed to the user.

Furthermore, in the second embodiment the second edge cover pieces 41*b* are bonded to the first material 3*a* of the laminate material piece 27 and to the topsheet 33. However, instead of being bonded to the topsheet 33, the second edge cover pieces 41*b* may be bonded to any other suitable component of the produced absorbent article positioned outside the first and second material edges 23, 24 and optionally outside the third material edges 25. The second edge cover pieces 41*b* may be bonded to the laminate material piece 27 and to the topsheet 33 or any other components by means of any suitable adhesive or by means of, for example, heat bonding, ultrasonic bonding or mechanical bonding.

Figure 4A:
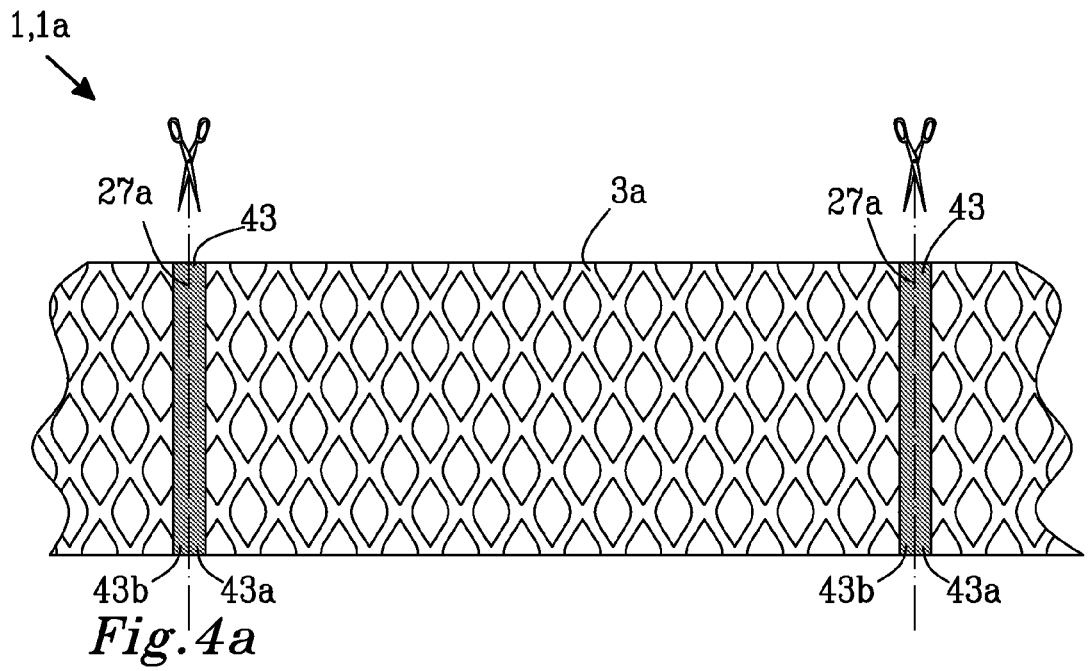
FIG. 4a shows a top view of a portion of the final laminate material web with applied protective pieces before cutting in accordance with the third embodiment.
Figure 4B:
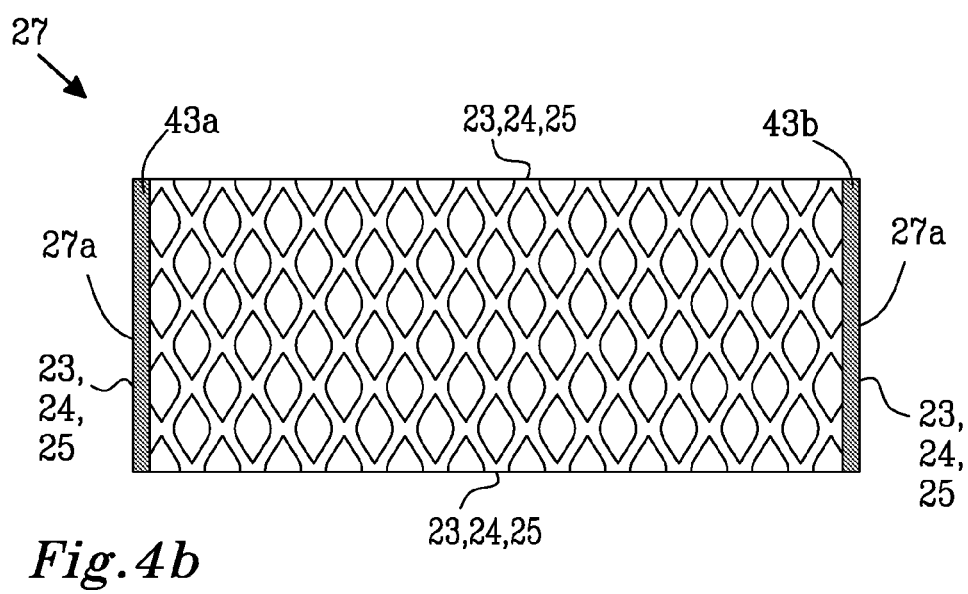
FIG. 4b shows a top view of the portion of the web shown in FIG. 4a after cutting.

A third embodiment of the method for producing an absorbent article corresponds to the second embodiment except for concerning the fact that the provision of the second edge cover arrangement 41*b* (FIG. 3*d*) is omitted. In addition, the step of producing the laminate material piece 27 of the laminate material web 1 by cutting along the two transverse cutting lines 27*a* is preceded by a step of providing two protective pieces 43 of a protective material and a step of attaching each protective piece 43 to the first material 3*a* of the laminate material web 1 over at least an area of the first material 3*a* corresponding to one of the cutting lines 27*a* (FIG. 4*a*). The cutting is then performed through the protective pieces 43 and the laminate material web 1 along the cutting lines 27*a* in order to produce the laminate material piece 27, whereby each protective piece 43 is divided into two parts 43*a*, 43*b* by the cutting (FIG. 4*b*). Thus, the produced laminate material piece 27 includes one part 43*a*, 43*b* of each protective piece 43 attached to the first material 3*a*. The protective pieces 43 are arranged to protect the web 1 from being ripped up during cutting. The protective pieces 43 are bonded to the first material 3*a* by means of e.g. an adhesive or by means of, for example, heat bonding, ultrasonic bonding or mechanical bonding. FIG. 4*a* shows a top view of a portion of the laminate material web 1 with applied protective pieces 43 before cutting and FIG. 4*b* shows a top view of the portion of the web 1 shown in FIG. 4*a* after cutting.

Figure 4C:
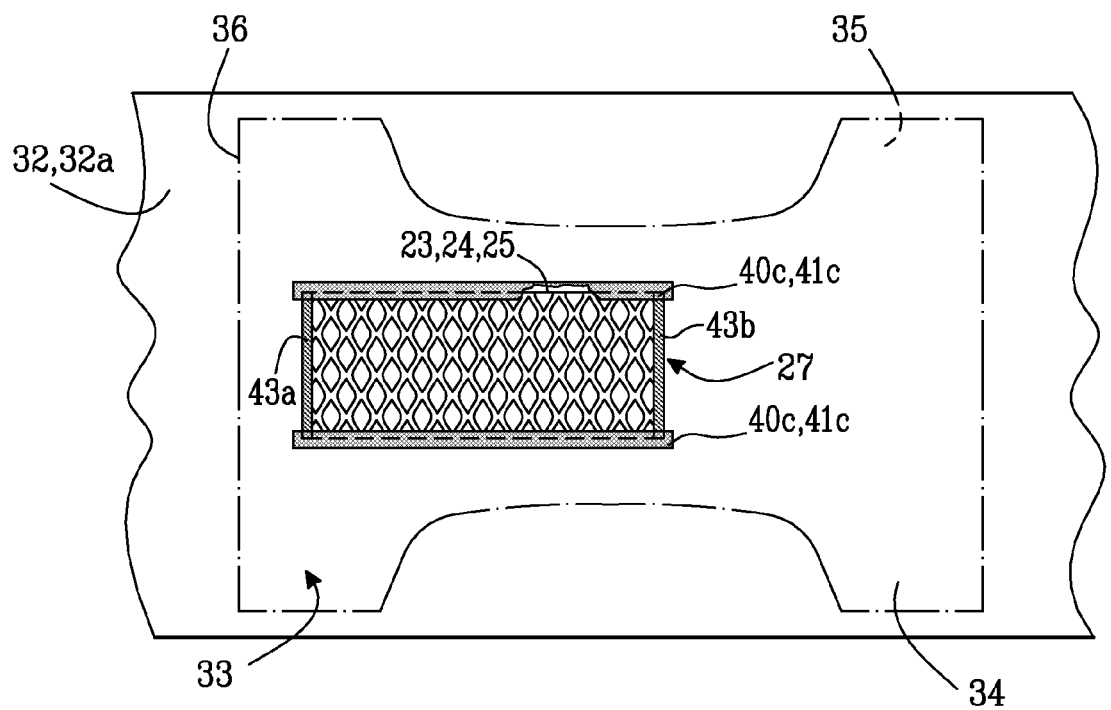
FIG. 4c is a top view of the portion of the web shown in FIG. 2d after application of the laminate material piece shown in FIG. 4b and after application of a third edge cover arrangement.

The laminate material piece 27 is applied to the first surface 34 of the topsheet 33 such that the first material 3*a* of the laminate material piece 27 is arranged to face the user and the third material 17*a* is arranged to be in contact with the topsheet 33. In addition, the laminate material piece 27 is produced to have such a size and shape and is subsequently applied to the first surface 34 of the topsheet 33 such that it extends within the borders 36 of the topsheet 33 (FIG. 4*c*). The laminate material piece 27 is applied such that it is at least positioned in that part of the produced absorbent article that constitutes the fecal receiving area.

Furthermore, in the third embodiment a third edge cover arrangement 40*c* including two third edge cover pieces 41*c* of an edge cover material is provided. Each third edge cover piece 41*c* is applied such that first material edges 23, second material edges 24 and third material edges 25 of the laminate material piece 27 being non-cut by means of the cutting are covered by the third edge cover arrangement 40*c* and are arranged to be non-exposed to the user. Each third edge cover piece 41*c* is applied such that it is partly positioned adjacently over the laminate material piece 27 and partly positioned adjacently over the topsheet 33. Thus, each third edge cover piece 41*c* is sized and positioned such that first material edges 23, second material edges 24 and third material edges 25 being non-cut during the step of cutting are covered by the third edge cover arrangement 40*c* and are arranged to be non-exposed to the user. FIG. 4*c* is a top view of a portion of the web 32 shown in FIG. 2*d* after application of the laminate material piece 27 to the first surface 34 of the topsheet 33 and after application of the third edge cover arrangement 40*c*. As shown in FIG. 4*c* the third edge cover pieces 41*c* may be strip-shaped. As also shown in FIG. 4*c* the third edge cover pieces 41*c* may overlap the protective pieces 43 in certain areas.

The third embodiment of the method for producing an absorbent article 2 may be varied in that the third edge cover arrangement 40*c* includes any other suitable number of third edge cover pieces 41*c* than two. In addition, the third embodiment may be varied in that the laminate material web 1 is produced such that the third material 17*a* extends outside the longitudinal first material edges 23 and the longitudinal second material edges 24 of the laminate material web 1 such that the web 1 includes two longitudinal portions of non-laminated third material 26 (FIG. 1*e*). In the variants of the third embodiment, the non-laminated third material 26 is not folded and bonded to the first material 3*a* as in the first embodiment. Thus, the third material 17*a* of the laminate material piece 27 produced by means of the cutting along the two transverse cutting lines 27*a* extends then outside the longitudinal first material edges 23 and the longitudinal second material edges 24 of the produced laminate material piece 27 (not shown). The third edge cover arrangement 40*c* may then be produced and applied such that those first, second and third material edges 23, 24, 25 of the laminate material piece 27, which are non-cut during the step of cutting the laminate material piece 27, are covered by the third edge cover arrangement 40*c* or such that only those first and second material edges 23, 24, which are non-cut during the step of cutting the laminate material piece 27, are covered by the third edge cover arrangement 40*c*.

Furthermore, in FIGS. 4*a*-*c* the produced laminate material piece 27 has a rectangular shape. However, the produced laminate material piece 27 may have any suitable shape, such as, for example, oval, heart-shaped or square-shaped. Depending on, for example, the shape of the laminate material piece to produce, the laminate material piece may be produced by cutting through the thickness of the laminate material web 1 in the thickness direction Z along one or more cutting lines, which may have any suitable shape. In case the laminate material piece 27 is produced to have another shape than that shown in FIGS. 4*a*-*c*, it may have other numbers of first material edges, second material edges and third material edges than those shown in FIGS. 4*a*-*c*.

The third embodiment or any alternative thereof may also be varied in that other numbers of protective pieces 43 than two are provided and utilized for protection during cutting of the laminate material piece 27 from the web 1, e.g. depending on the shape of the laminate material piece 27 to produce and the number of cutting lines utilized. However, in each case at least one protective piece 43 of a protective material is provided and each protective piece 43 is applied to the first material 3*a* of the web 1 over at least an area of the first material 3*a* corresponding to one of the cutting lines 27*a* before the cutting. The cutting is performed through the protective piece 43 and the web 1 along each cutting line 27*a* and the respective protective piece 43 is divided into two parts 43*a*, 43*b* by the cutting.

In all variants of the third embodiment, the third edge cover arrangement 40c includes at least one third edge cover piece 41c and each third edge cover piece 41c is applied such that at least first and second material edges 23, 24 of the laminate material piece 27 being non-cut by means of the cutting are covered by the third edge cover arrangement 40c and are arranged to be non-exposed to the user.

Furthermore, in the third embodiment the third edge cover pieces 41c are bonded to the first material 3a of the laminate material piece 27 and to the topsheet 33. However, instead of being bonded to the topsheet 33, the third edge cover pieces 41c may be bonded to any other suitable component of the produced absorbent article positioned outside the first and second material edges 23, 24 and optionally outside the third material edges 25. The third edge cover pieces 41c may be bonded to the laminate material piece 27 and to the topsheet 33 or any other components by means of any suitable adhesive or by means of, for example, heat bonding, ultrasonic bonding or mechanical bonding.

The protective material is a material that protects the web 1 from being ripped up during cutting. Examples of suitable materials for use as the protective material are different types of nonwoven materials, such as spunbond webs, meltblown webs, carded webs, thermobonded webs, through-air-bonded webs, etc. The nonwoven materials may be made of, for example, polypropylene, polyethylene, polyester or bicomponent fibres. Also, the protective material may be a laminate or a film material. Preferably, but not necessarily, the protective material is hydrophobic.

A fourth embodiment of the method for producing an absorbent article corresponds to the second embodiment except for concerning the fact that a fourth edge cover arrangement 40d and two barrier flap members 42 (FIGS. 5a-b) are utilized instead of the second edge cover arrangement 40b (FIGS. 3d-e) for covering the first, second and third material edges 23, 24, 25 of the laminate material piece 27. Thus, in the fourth embodiment the laminate material piece 27 is produced to have such a size and shape and is applied to the first surface 34 of the topsheet 33 such that it extends within the borders 36 of the topsheet 33. The laminate material piece 27 is applied such that it is at least positioned in that part of the produced absorbent article that constitutes the fecal receiving area.

Figure 5A:
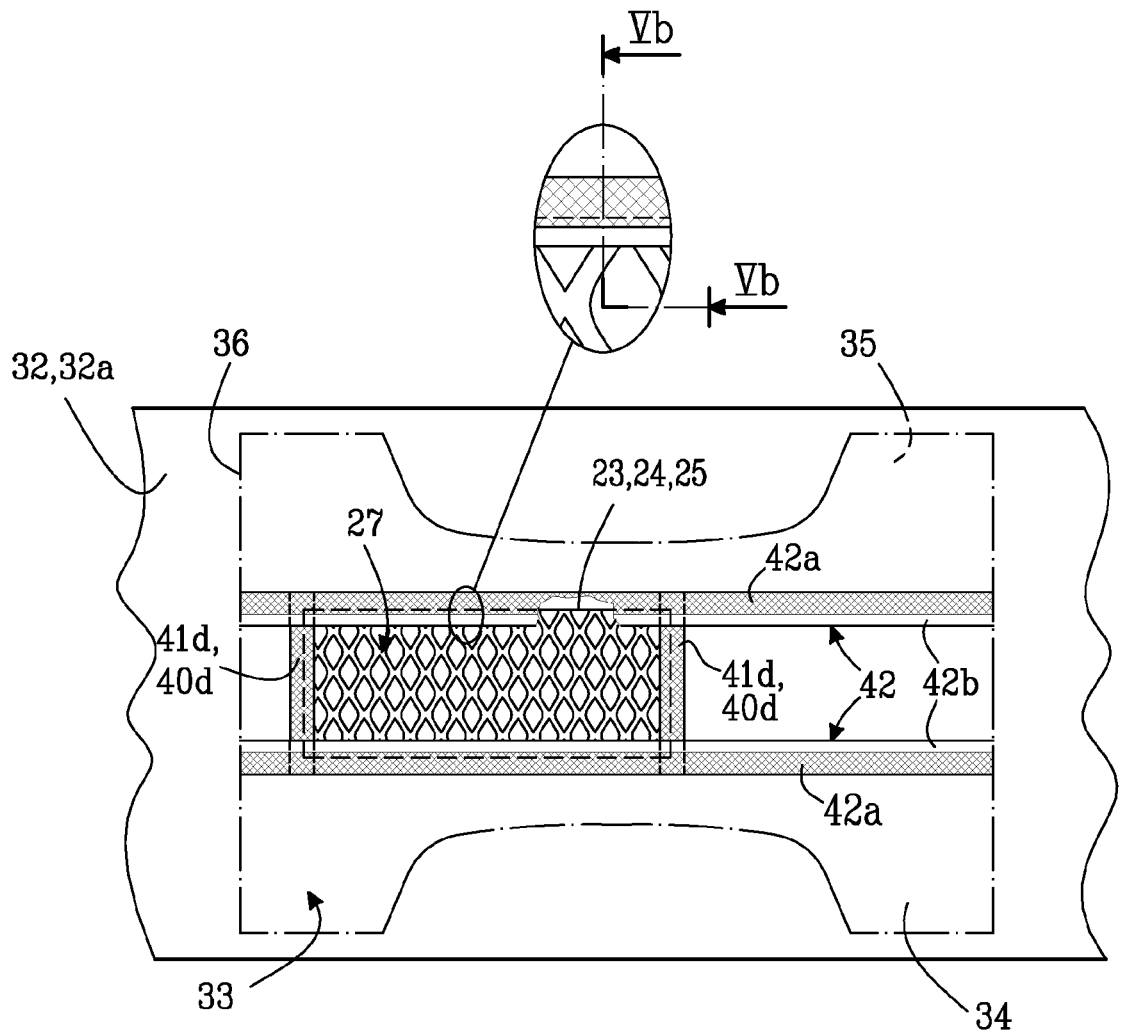
FIG. 5a shows a top view of the portion of the web shown in FIG. 3d after application of a fourth edge cover arrangement and two barrier flap members in the fourth embodiment.
Figure 5B:
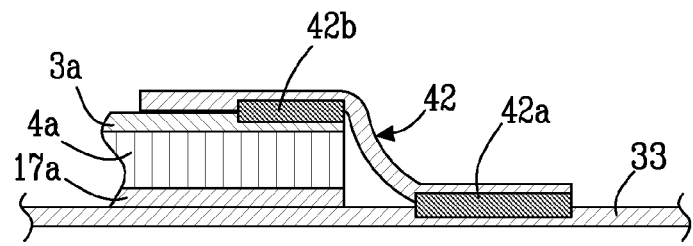

Furthermore, two barrier flap members 42a and a fourth edge cover arrangement 40d including two fourth edge cover pieces 41d are provided in the fourth embodiment (FIGS. 5a-b). Each barrier flap member 42 includes an attachment region 42a for attachment to other components and a non-attachment region 42b including an elastic member (not shown in FIGS. 5a-b) for spacing parts of the barrier flap member 42 from the topsheet 33. This will be further described below. The barrier flap members 42 form leakage barriers of the absorbent article.

In the fourth embodiment, the fourth edge cover arrangement 40d and the barrier flap members 42 are applied such that the first, second and third material edges 23, 24, 25 of the laminate material piece 27 are covered by the combination of the fourth edge cover arrangement 40d and the attachment regions 42a of the barrier flap members 42 and such that the first, second and third material edges 23, 24, 25 of the laminate material piece 27 are arranged to be non-exposed to the user.

As shown in FIG. 5a each fourth edge cover piece 41d is applied such that it is partly positioned adjacently over the laminate material piece 27 and partly positioned adjacently over the topsheet 33. Each barrier flap member 42 is applied such that the attachment region 42a thereof is partly positioned adjacently over the laminate material piece 27 and partly positioned adjacently over the topsheet 33. FIG. 5a shows a top view of the portion of the web 32 shown in FIG. 2d after application of the fourth edge cover arrangement 40d and the two barrier flap members 42. FIG. 5b is a cross-sectional view according to line Vb-Vb in FIG. 5a.

Thus, the fourth edge cover pieces 41d of the fourth edge cover arrangement 40d and the attachment regions 42a of the barrier flap members 42 cover together all first material edges 23, all second material edges 24 and all third material edges 25 of the laminate material piece 27 after application so as to avoid contact thereof with the user. As shown in FIG. 5a the fourth edge cover pieces 41d may be strip-shaped. As also shown in FIG. 5a the fourth edge cover pieces 41d and the barrier flap members 42 may overlap each other in certain areas.

The fourth embodiment of the method for producing an absorbent article 2 may be varied in that the fourth edge cover arrangement 40d includes more than two fourth edge cover pieces 41d. In addition, the fourth embodiment may be varied in that the laminate material web 1 is produced such that the third material 17a extends outside the longitudinal first material edges 23 and the longitudinal second material edges 24 of the laminate material web 1 such that the web 1 includes two longitudinal portions of non-laminated third material 26 (FIG. 1e). In the variants of the fourth embodiment, the non-laminated third material 26 is not folded and bonded to the first material 3a as in the first embodiment. Thus, the third material 17a of the laminate material piece 27 produced by means of the cutting along the two transverse cutting lines 27a extends then outside the longitudinal first material edges 23 and the longitudinal second material edges 24 of the produced laminate material piece 27 (not shown). The fourth edge cover arrangement 40d and the barrier flap members 42 may then be applied such that the first, second and third material edges 23, 24, 25 of the laminate material piece 27 are covered or such that only the first and second material edges 23, 24 of the laminate material piece 27 are covered by the fourth edge cover arrangement 40d and the attachment regions 42a of the barrier flap members 42.

Furthermore, in FIGS. 5a-b the produced laminate material piece 27 has a rectangular shape. However, the produced laminate material piece 27 may have any suitable shape, such as, for example, oval, heart-shaped or square-shaped. Depending on, for example, the shape of the laminate material piece to produce, the laminate material piece may be produced by cutting through the thickness of the laminate material web 1 in the thickness direction Z along one or more cutting lines, which may have any suitable shape. In case the laminate material piece 27 is produced to have another shape than that shown in FIGS. 5a-b, it may have other numbers of first material edges, second material edges and third material edges than those shown in FIGS. 5a-b.

In all variants of the fourth embodiment, the fourth edge cover arrangement 40d includes at least two fourth edge cover pieces 41d, and the fourth edge cover pieces 41d and the barrier flap members 42 are applied such that at least all first material edges 23 and all second material edges 24 of the laminate material piece 27 are covered by the combination of the fourth edge cover arrangement 40d and the attachment regions 42a of the barrier flap members 42 and are arranged to be non-exposed to the user.

Furthermore, in the fourth embodiment the fourth edge cover pieces 41d and the attachment regions 42a of the barrier flap members 42 are bonded to the first material 3a of the laminate material piece 27 and the topsheet 33. However, instead of being bonded to the topsheet 33, the fourth edge cover pieces 41d and the attachment regions 42a of the barrier flap members 42 may be bonded to any other suitable component of the produced absorbent article positioned outside the first and second material edges 23, 24 and optionally outside the third material edges 25. The fourth edge cover pieces 41d and the barrier flap members 42 may be bonded to the laminate material piece 27 and to the topsheet 33 or any other components by means of any suitable adhesive or by means of, for example, heat bonding, ultrasonic bonding or mechanical bonding.

The edge cover material utilized in any of the above described embodiments is a material that is suitable for covering the first, second and third material edges 23, 24, 25 of the laminate material piece 27 in order to reduce the risk that the borders 23, 24, 25 are ripped up due to contact with the skin of the user. Examples of suitable materials for use as the edge cover material are different types of nonwoven materials, such as spunbond webs, meltblown webs, carded webs, thermobonded webs, through-air-bonded webs, etc. The nonwoven materials may be made of, for example, polypropylene, polyethylene, polyester or bicomponent fibres. Also, the edge cover material may be a laminate or a film material. Preferably, but not necessarily, the edge cover material is hydrophobic.

A fifth embodiment of the method for producing an absorbent article corresponds to the second embodiment except for concerning the fact that an aperture 37 (FIG. 6a) is produced in the topsheet 33 before application of the laminate material piece 27 to the topsheet 33 and that the laminate material piece 27 is applied to the second surface 35 of the topsheet 33 instead of to the first surface 34 of the topsheet 33. In addition, the second edge cover arrangement 40b utilized in the second embodiment is not utilized in the fifth embodiment.

Thus, in accordance with the second embodiment, the laminate material web 1 is produced in the fifth embodiment such that the third material 17a does not extend outside the longitudinal first material edges 23 and the longitudinal second material edges 24 of the laminate material web 1 in accordance with FIG. 1d. In addition, the laminate material piece 27 is produced by cutting along two transverse cutting lines 27a. Thereby, the third material 17a of the produced laminate material piece 27 does not extend outside longitudinal first material edges 23 and the longitudinal second material edges 24 of the produced laminate material piece 27 in accordance with FIG. 3a.

Figure 6A:
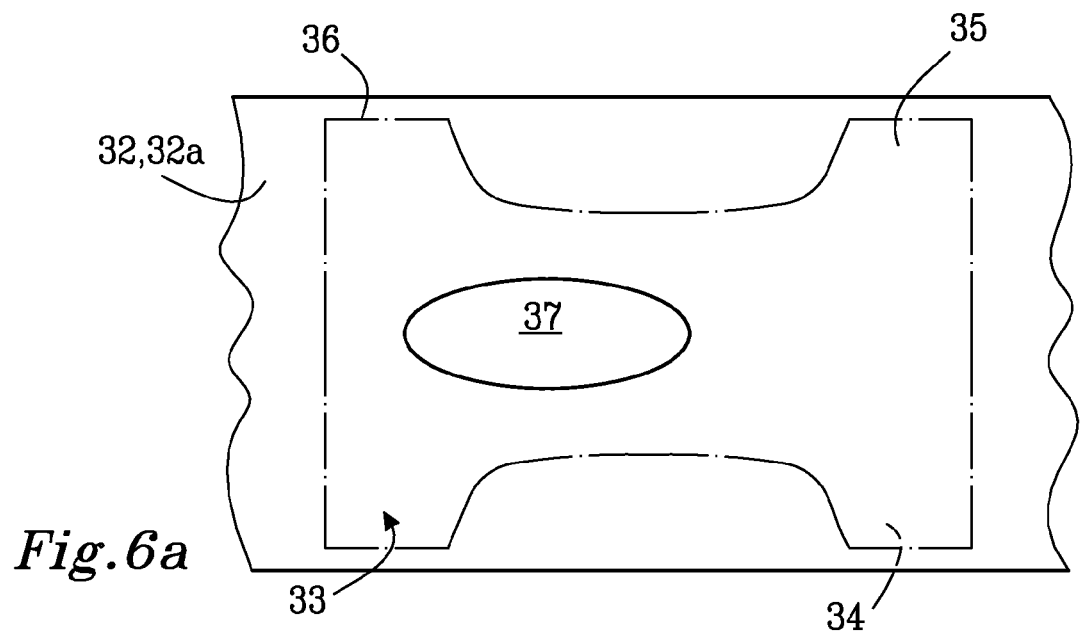
FIG. 6a is a top view of the portion of the web shown in FIG. 2d with an aperture produced in the fifth embodiment.

Furthermore, in the fifth embodiment, an aperture 37 is produced in the topsheet 33. FIG. 6a shows a portion of the web 32 of the topsheet material 32a with the produced aperture 37. In FIG. 6a the aperture 37 has an oval shape. However, the aperture 37 may have any suitable shape. Also, any suitable means may be utilized for producing the aperture 37. The aperture may, for example, be produced by means of a rotary cutting knife.

The aperture 37 is provided such that it is at least positioned in that part of the produced absorbent article that constitutes the fecal receiving area, which is the area that immediately surrounds the point of the absorbent article that is positioned opposite to the user's anus.

In the fifth embodiment, the produced laminate material piece 27 is applied to the second surface 35 of the topsheet 33 after production of the aperture 37, whereby the laminate material piece 27 is applied to the second surface 35 such that the first material 3a is arranged to face the user and such that a plurality of the openings 15 of the laminate material piece 27 are arranged to be exposed to the user through the aperture 37.

More specifically, in the fifth embodiment the laminate material piece 27 is produced to have such a size and shape and is applied to the second surface 35 of the topsheet 33 such that it at least covers the aperture 37, such that at least some of the openings 15 of the laminate material piece 27 are arranged to be exposed to the user through the aperture 37 and such that all first material edges 23, all second material edges 24 and all third material edges 25 of the laminate material piece 27 are arranged to be non-exposed to the user through the aperture 37.

Thus, in the fifth embodiment, the laminate material piece 27 is produced and applied to the second surface 35 of the topsheet 33 such that it extends over the aperture 37 and such that parts of the first material 3a is positioned in contact with the second surface 35 of the topsheet 33.

Figure 6B:
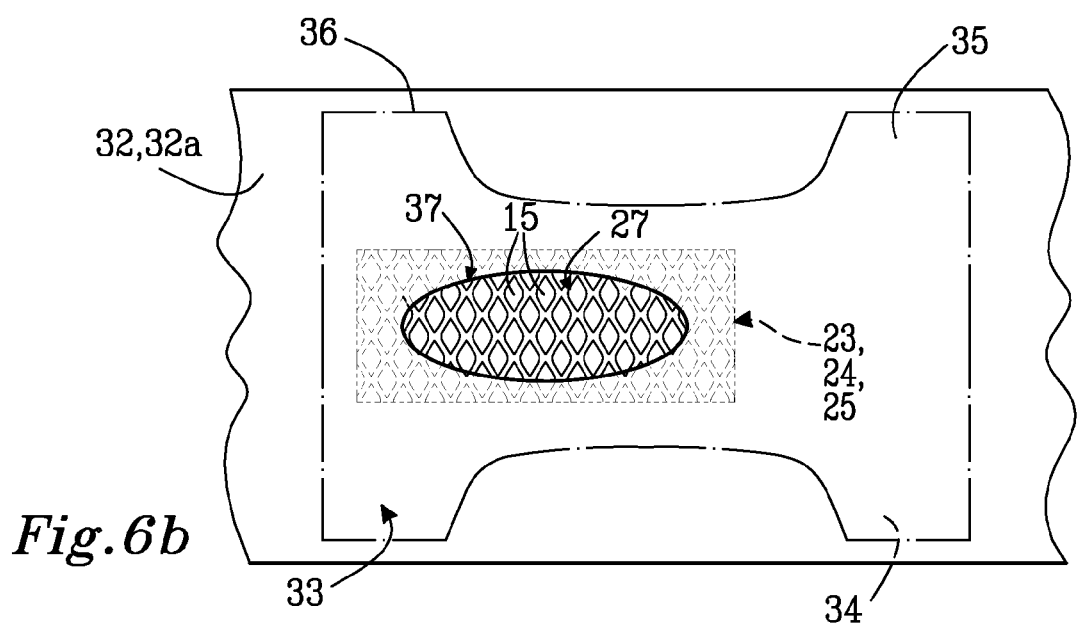
FIG. 6b shows a top view of the portion of the web shown in FIG. 6a after application of a laminate material piece.

FIG. 6b shows a portion of the web 32 after application of the laminate material piece 27 seen from a user-facing side of the topsheet 33, i.e. with the first surface 34 of the web 32 being located uppermost. As may be seen in FIG. 6b, the fact that the first material edges 23, the second material edges 24 and the third material edges 25 are arranged to be non-exposed to the user through the aperture 37 imply that they are covered by the topsheet 33 when seen from a user-facing side of the topsheet 33. The non-exposure to the user implies that the risk that material parts in the first, second and/or third material edges 23, 24, 25 are ripped due to contact with the skin of the user is avoided. Another advantage with the embodiment shown in FIG. 6b is that an accumulating pocket is formed under the edge of the topsheet material. In addition, an appealing appearance is provided.

As mentioned above, in the fifth embodiment the laminate material web 1 is produced such that the third material 17a does not extend outside the longitudinal first material edges 23 and the longitudinal second material edges 24 of the laminate material web 1 (FIG. 1d). However, the laminate material web 1 may alternatively be produced such that the third material 17a extends outside the longitudinal first material edges 23 and the longitudinal second material edges 24 of the laminate material web 1 (FIG. 1e). Then the third material 17a of the laminate material piece 27 produced by means of the cutting along the two transverse cutting lines 27a extends outside the longitudinal first material edges 23 and the longitudinal second material edges 24 of the produced laminate material piece 27 (not shown). However, in all cases the produced laminate material piece 27 is sized and applied to the second surface 35 of the topsheet 33 such that all first, second and third material edges 23, 24, 25 of the produced laminate material piece 27 are arranged to be non-exposed to the user through the aperture 37.

Furthermore, in FIGS. 6a-b the produced laminate material piece 27 has a rectangular shape. However, the produced laminate material piece 27 may have any suitable shape, such as, for example, oval, heart-shaped or square-shaped. Depending on, for example, the shape of the laminate material piece to produce, the laminate material piece may be produced by cutting through the thickness of the laminate material web 1 in the thickness direction Z along one or more cutting lines, which may have any suitable shape. In case the laminate material piece 27 is produced to have another shape than that shown in FIGS. 6a-b, it may have other numbers of first material edges, second material edges and third material edges than those shown in FIGS. 6a-b.

In general, in the method for producing an absorbent article, the laminate material web 1 is produced in accordance with any of the embodiments or variants described above of the method for producing the laminate material web 1. A piece 27 of the web 1 of the laminate material 1a is produced by cutting along at least one cutting line 27a, whereby the laminate material piece 27 is produced such that it includes a plurality of the openings 15. A liquid permeable topsheet 33 for the absorbent article 2 is provided. The topsheet 33 has a first surface 34 arranged to face the user and a second surface 35 arranged to face away from the user. The topsheet 33 is delimited by borders 36. The laminate material piece 27 is applied to the topsheet 33 such that the first material 3a of the laminate material piece 27 is arranged to face the user and such that a plurality of the openings 15 of the laminate material piece 27 are arranged to be exposed to the user.

Figure 7B:
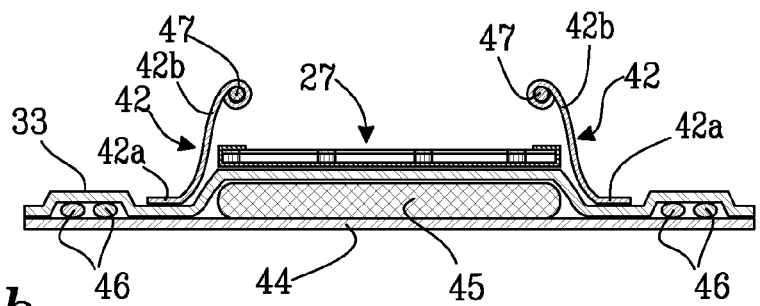

All embodiments and variants of the method for producing an absorbent article include steps for providing further necessary components and optional components for forming the complete absorbent article. One example of a complete absorbent article 2 in the form of a diaper produced by means of the method is shown in FIGS. 7a-b. More specifically, the absorbent article 2 shown in FIGS. 7a-b has been produced by utilizing the first embodiment of the method for producing the absorbent article.

Thus, the absorbent article 2 shown in FIGS. 7a-b includes the liquid permeable topsheet 33 and the laminate material piece 27 with applied first edge cover pieces 41a shown in FIG. 2f. In addition, the absorbent article 2 includes a liquid impermeable backsheet 44 and an absorbent core 45. The absorbent core 45 is enclosed by the topsheet 33 and the backsheet 44. The topsheet 33 and the backsheet 44 extend outwardly beyond the peripheral edges of the absorbent core 45, and have their surfaces bonded to each other, e.g. by gluing or welding by heat or ultrasonic treatment. The topsheet 33 and the backsheet 44 may further be bonded, e.g. by adhesive, to the absorbent core 45.

The absorbent article 2 has a longitudinal direction Y and a transverse direction X when positioned in a plane state and is divided into a front portion 49 and a rear portion 50 in the longitudinal direction Y. The front portion 49 and the rear portion 50 are constituted by the two parts formed when the absorbent article 2 is folded along a middle transverse line, i.e. a transverse line located at a middle position of the absorbent article 2 in the longitudinal direction Y.

Furthermore, the absorbent article 2 shown in FIGS. 7a-b includes first elastic members 46 adjacent the leg openings. The first elastic members 46 are bonded between the topsheet 33 and the backsheet 44 in a stretched condition so as to provide elasticized leg openings of the absorbent article 2. The first elastic members 46 may alternatively be of a material that is activatable by some means, for example by heat, to an elastified state, whereby they may be attached to the article 2 in an unstretched inactivated state and are subsequently activated to a contracted elastic state.

The absorbent article 2 is further provided with elastic barrier flap members 42 having a proximal edge and a distal edge. Each barrier flap member 42 has an attachment region 42a in which the barrier flap member 42 is attached to the topsheet 33 and a non-attachment region 42b in which the barrier flap member 42 is non-attached to the topsheet 33. The attachment region 42a is located at a proximal edge of the barrier flap member 42 and the non-attachment region 42b is located at a distal edge of the barrier flap member 42. In addition, a second elastic member 47 is comprised in the non-attachment region 42b of each barrier flap member 42. The second elastic member 47 is contractably attached at the non-attachment region 42b for spacing parts of the barrier flap member 42 from the topsheet 33. Alternatively, the second elastic members 47 are of the activatable kind as described above, whereby they may be attached to the barrier flap members 42 in an uncontracted position and be activated subsequently. The barrier flap members 42 form leakage barriers.

In addition, the absorbent article 2 is provided with fasteners 48 attached thereto. The fasteners 48 are intended to be fastened to the front portion 49 of the absorbent article 48 to form a pant-like shape. The fasteners 48 may be in the form of adhesive tapes or hook elements adapted to attach to a loop material, for example in the form of a nonwoven material associated with the topsheet 33 or a nonwoven material forming the topsheet 33 of the absorbent article 2.

Thus, the method for producing an absorbent article 2 according to any of the above described embodiments or variants includes further a step of providing a liquid permeable backsheet 44, a step of providing an absorbent core 45 and a step of assembling the backsheet 44, the absorbent core 45 and the topsheet 33 so as to form the absorbent article 2. These steps may be performed in any suitable way known in the art.

In case the method involves applying the laminate material piece 27 on the first side 34 of the topsheet 33 (as in the first to fourth embodiments described above), the backsheet 44, the absorbent core 45 and the topsheet 33 may be assembled before or after the laminate material piece 27 is applied to the topsheet 33. In case the method involves forming an aperture 37 in the topsheet 33 and applying the laminate material piece 27 on the second side 35 of the topsheet 33 (as in the fifth embodiment described above), the topsheet 33 is assembled with the absorbent core 45 and the backsheet 44 after provision of the aperture 37 and application of the laminate material piece 27. Optionally, the method for producing an absorbent article 2 includes further steps for providing and attaching barrier flap members 42, first elastic members 46 and/or fasteners 48 as described above or any other components.

As mentioned above, the method for producing the absorbent article 2 includes a step of cutting the topsheet 33 from the web 32 along cutting lines corresponding to the borders 36. This step may be performed before or after assembly with other components.

In use of the absorbent article produced by means of the method, the topsheet 33 is placed in contact with the skin of a user. The liquid permeable topsheet material 32a of the topsheet 33 may include apertures through which liquid can permeate, or alternatively, liquid may permeate through the spaces between individual fibres. It may be any material used for this purpose, for example a nonwoven material, such as a spunbond material of continuous filaments, a meltblown material, a thermobonded fibrous web such as a carded fibrous web, a hydroentangled material, a wetlaid material, etc. The topsheet material 32a may include many different types of fibres. For example, natural fibres such as wood pulp or cotton fibres, jute, wool and hair fibres may be used. Man-made fibres, such as e.g. polyester, viscose, nylon, polypropylene, and polyethylene may also be used, polypropylene and polyester being preferred. Mixtures of different fibres types may also be used, e.g. a 50/50 mix of polyester and viscose. Bicomponent fibres or binder fibres may also be used. The topsheet may also be a layer of so called tow fibres bonded in a bonding pattern, as e.g. disclosed in EP-A-1 035 818, or a perforated plastic film. The materials suited as top sheet materials should be soft and non-irritating to the skin and intended to be readily penetrated by body liquid, e.g. urine or menstrual liquid. The topsheet material may be different in different regions of the topsheet 33.

The topsheet material 32a may be treated with a chemical agent to improve one or more of its properties. For example, treatment of the topsheet with surfactants will make it more liquid-permeable. Treatment of the topsheet with a lotion, e.g. as described in EP1227776 provides a softer, more comfortable feel to the wearer, and improved skin properties.

Furthermore, the topsheet material 32*a* may include at least two separate but interconnected layers. Each layer may include the same materials or may include different materials with different properties as regards e.g. strength, stiffness, liquid or gas permeability. Each layer may also be a laminate of two or more sub-layers.

The absorbent core 45 may be of any conventional kind. Examples of commonly occurring absorbent materials are cellulosic fluff pulp, tissue layers, airlaid cellulose material, highly absorbent polymers (so called superabsorbents), absorbent foam materials, absorbent nonwoven materials or the like. It is common to combine cellulosic fibers with superabsorbents in an absorbent core. It is also common to have absorbent cores including layers of different material with different properties with respect to liquid acquisition capacity, liquid distribution capacity and storage capacity. This is well-known to the person skilled in the art and does therefore not have to be described in detail. The thin absorbent cores, which are common in today's absorbent articles, often include a compressed mixed or layered structure of cellulosic fibres and superabsorbent material. The size and absorbent capacity of the absorbent core may be varied to suit different uses.

The backsheet material of the backsheet 44 may include a thin plastic film, e.g. a polyethylene or polypropylene film, a nonwoven material coated with a liquid impervious material, a hydrophobic nonwoven material which resists liquid penetration, or a laminate of plastic films and nonwoven materials. The backsheet material may be breathable so as to allow vapour to escape from the absorbent core 45, while still preventing liquids from passing through the backsheet material. The backsheet material may be elastic. The material of the backsheet may be different in different regions of the backsheet 44.

In all embodiments of the method for producing an absorbent article, the laminate material piece 27 is produced and applied to the topsheet 33 such that it is comprised in at least a fecal receiving area of the produced absorbent article, i.e. such that a plurality of the openings 15 of the laminate material piece 27 are exposed to the user in the fecal receiving area. As mentioned above, the fecal receiving area is the area that immediately surrounds the point of the absorbent article that is positioned opposite to the user's anus. The fecal receiving area is comprised in the rear portion 50 of the absorbent article 2. Thus, the laminate material piece 27 may, for example, be sized and positioned such that it is only located in the rear portion 50 or such that it is located in both the rear portion 50 and the front portion 49.

The absorbent article produced by means of any of the embodiments of the method is especially effective in handling and retaining low-viscosity fecal material, which is prevalent in younger children, especially those who are breast fed, and also in users having diarrhea. Such low-viscosity fecal material easily moves around on the body facing side of the topsheet and increases the risk for leakage, and further smears it against the skin of the user making cleanup more difficult. Since the absorbent article produced by means of any of the embodiments of the method includes the laminate material piece 27 in at least the fecal receiving area and since a plurality of the openings 15 are arranged to be exposed to the user, improved immobilization of low-viscosity fecal material is obtained.

Low-viscosity fecal material (as well as more solid forms of fecal material) may move into the exposed openings 15, which together with the third material 17*a* covering the openings 15 on the garment facing side form containment wells. Fecal material comprised within the openings 15 is spaced apart from the user's skin, whereby smearing of fecal material against the skin of the user is reduced. In addition, fecal material comprised within the openings 15 is inhibited from moving around on the topsheet 33. Thus, the openings 15 imply that the immobilization of fecal material (i.e. the retaining of fecal material) is improved and that the risk of leakage of fecal material is reduced.

Embodiments of the invention have been described with reference to the embodied figures. However, the invention is not limited to the above-described embodiments alone. Features from one or more of the above embodiments may be combined as required, and the ultimate scope of the invention should be understood as being defined in the appended claims.

The invention claimed is:

1. A method for producing a web of a laminate material for retaining faeces for use in an absorbent article comprising the steps of:
   providing a first web of a first material for contacting the skin of a user of said absorbent article;
   providing a second web of a second material, said second material being a volume-forming material;
   laminating said first web and said second web so as to form an intermediate laminate web, said intermediate laminate web having a longitudinal direction, a transverse direction and a thickness direction;
   providing a multitude of transversal slits in said intermediate laminate web, each slit extending through said first material and said second material of said intermediate laminate web in said thickness direction;
   expanding said intermediate laminate web in said longitudinal direction such that said slits are opened to openings for retaining faeces, whereby said expansion provides an expanded intermediate laminate web in the form of a reticulated structure,
   providing a third web of a third material for fixing said expanded intermediate laminate web such that it is maintained in an expanded state, and
   laminating said second material of said expanded intermediate laminate web and said third web, whereby said expanded intermediate laminate web is fixed in position in relation to said third web and is fixed in an expanded state, and whereby said laminate material web is formed,
   wherein said first material of said produced laminate material web comprises two longitudinal first material edges and said second material of said produced laminate material web comprises two longitudinal second material edges,
   wherein said third material of said produced laminate material web extends outside said longitudinal first material edges and said longitudinal second material edges such that said third material of said laminate material web comprises two longitudinal portions of non-laminated third material, and
   wherein said method for producing said laminate material web further comprises the step of:
   folding and bonding said non-laminated third material of said produced laminate material web to said first material so as to cover at least said longitudinal first material edges and said longitudinal second material edges of said laminate material web by said non-laminated third material.

2. A method for producing an absorbent article comprising the steps of:

providing a first web of a first material for contacting the skin of a user of said absorbent article;

providing a second web of a second material, said second material being a volume-forming material;

laminating said first web and said second web so as to form an intermediate laminate web, said intermediate laminate web having a longitudinal direction, a transverse direction and a thickness direction;

providing a multitude of transversal slits in said intermediate laminate web, each slit extending through said first material and said second material of said intermediate laminate web in said thickness direction;

expanding said intermediate laminate web in said longitudinal direction such that said slits are opened to openings for retaining faeces, whereby said expansion provides an expanded intermediate laminate web in the form of a reticulated structure, providing a third web of a third material for fixing said expanded intermediate laminate web such that it is maintained in an expanded state, and laminating said second material of said expanded intermediate laminate web and said third web, whereby said expanded intermediate laminate web is fixed in position in relation to said third web and is fixed in an expanded state, and whereby a laminate material web is formed;

producing a piece of said laminate material web by cutting along at least one cutting line, whereby said laminate material piece is produced such that it comprises a plurality of said openings, providing a liquid permeable topsheet for said absorbent article, said topsheet having a first surface arranged to face said user and a second surface arranged to face away from said user, said topsheet being delimited by borders, and applying said laminate material piece to said topsheet such that said first material of said laminate material piece is arranged to face said user and such that at least a plurality of said openings of said laminate material piece are arranged to be exposed to said user.

3. A method for producing an absorbent article comprising the steps of:

producing said laminate material web according to the method according to claim 1, producing a piece of said laminate material web by cutting along at least one cutting line, whereby said laminate material piece is produced such that it comprises a plurality of said openings, providing a liquid permeable topsheet for said absorbent article, said topsheet having a first surface arranged to face said user and a second surface arranged to face away from said user, said topsheet being delimited by borders, applying said laminate material piece to said topsheet such that said first material of said laminate piece is arranged to face said user and such that at least a plurality of said openings of said laminate material piece are arranged to be exposed to said user, providing an edge cover arrangement comprising at least two edge cover pieces of an edge cover material, and applying each edge cover piece such that all first material edges and all second material edges of said laminate material piece are covered by a combination of said non-laminated third material and said edge cover arrangement and are arranged to be non-exposed to said user, wherein said step for producing said laminate material piece comprises cutting along two transverse cutting lines, wherein said step for applying said laminate material piece to said topsheet comprises applying said laminate material piece to said first surface, and wherein said laminate material piece is produced and applied to said first surface of said topsheet such that it extends within said borders of said topsheet.

4. The method for producing an absorbent article according to claim 2 further comprising the steps of:

providing an edge cover arrangement comprising at least one edge cover piece, and applying each edge cover piece such that at least all first material edges and all second material edges of said laminate material piece are covered by said edge cover arrangement and are arranged to be non-exposed to said user, wherein said step for applying said laminate material piece to said topsheet comprises applying said laminate material piece to said first surface, and wherein said laminate material piece is produced and applied to said first surface of said topsheet such that it extends within said borders of said topsheet.

5. The method for producing an absorbent article according to claim 2 further comprising the steps of:

providing an edge cover arrangement comprising at least one edge cover piece of an edge cover material, and applying each edge cover piece such that at least first material edges and second material edges of said laminate material piece being non-cut by said cutting are covered by said edge cover arrangement and arranged to be non-exposed to said user, wherein said step of producing a laminate material piece is preceded by the steps of:

providing at least one protective piece of a protective material; and applying each protective piece to said first material of said laminate material web over at least an area of said first material corresponding to one of said cutting lines before said cutting, whereby said cutting is performed through said protective piece and said laminate material web along each cutting line and whereby each protective piece is divided into two parts by said cutting, wherein said step for applying said laminate material piece to said topsheet comprises applying said laminate material piece to said first surface, and wherein said laminate material piece is produced and applied to said first surface of said topsheet such that it extends within said borders of said topsheet.

6. The method for producing an absorbent article according to claim 2 further comprising the steps of:

providing an edge cover arrangement comprising at least two edge cover pieces of an edge cover material, providing two barrier flap members, each barrier flap member having an attachment region, and applying said edge cover pieces and said barrier flap members such that at least all first material edges and all second material edges of said laminate material piece are covered by the combination of said edge cover arrangement and said attachment regions of said barrier flap members and are arranged to be non-exposed to said user, wherein said step for applying said laminate material piece to said topsheet comprises applying said laminate material piece to said first surface, wherein said laminate material piece is produced and applied to said first surface of said topsheet such that it extends within said borders of said topsheet.

7. The method for producing an absorbent article according to claim 2, wherein said method for producing an absorbent article further comprises a step of producing an aperture in said topsheet, wherein said step for applying said laminate material piece to said topsheet comprises applying said laminate material piece to said second surface, and wherein said laminate material piece is produced and applied to said second surface of said topsheet such that it at least covers said aperture, such that at least a plurality of said openings of said laminate material piece are arranged to be exposed to said user through said aperture, and such that all first material edges, all second material edges and all third material edges of said laminate material piece are arranged to be non-exposed to said user through said aperture.

8. An absorbent article obtained by a method according to claim 2.

* * * * *